United States Patent
Mazlish et al.

(10) Patent No.: US 10,610,643 B2
(45) Date of Patent: Apr. 7, 2020

(54) OCCLUSION RESOLUTION IN MEDICATION DELIVERY DEVICES, SYSTEMS, AND METHODS

(71) Applicant: Bigfoot Biomedical, Inc., Milpitas, CA (US)

(72) Inventors: Bryan Mazlish, Palo Alto, CA (US); Lane Desborough, Thousand Oaks, CA (US); Ravi Shankar Rontala Raghunathan, Union City, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 181 days.

(21) Appl. No.: 15/404,442

(22) Filed: Jan. 12, 2017

(65) Prior Publication Data

US 2017/0203036 A1    Jul. 20, 2017

Related U.S. Application Data

(60) Provisional application No. 62/278,974, filed on Jan. 14, 2016.

(51) Int. Cl.
*A61M 5/172* (2006.01)
*A61M 5/168* (2006.01)
(Continued)

(52) U.S. Cl.
CPC ............ *A61M 5/1723* (2013.01); *A61M 5/00* (2013.01); *A61M 5/16854* (2013.01);
(Continued)

(58) Field of Classification Search
CPC .... A61M 2005/16863; A61M 2205/18; A61M 2205/332; A61M 2205/3331;
(Continued)

(56) References Cited

U.S. PATENT DOCUMENTS 7,828,528 B2    11/2010   Estes et al.
7,833,196 B2    11/2010   Estes et al.
(Continued)

OTHER PUBLICATIONS

International Search Report and Written Opinion in Application No. PCT/US2017/013112, dated May 15, 2017, 9 pages.
(Continued)

*Primary Examiner* — Quynh-Nhu H. Vu
(74) *Attorney, Agent, or Firm* — Fish & Richardson P.C.

(57) ABSTRACT

Methods, devices, and systems of delivering infusion fluid (e.g., medication such as insulin) can detect, at multiple times during a dispensation period of time, a pressure level of the infusion fluid in an infusion fluid pathway, either directly or indirectly. Based on the detected pressure levels, one or more actual dispensation times that are after an intended dispensation time can be determined. In some cases, methods, devices, and systems provided herein can use variable occlusion alarm thresholds, which can depend on variables such as an age of an infusion set and/or a current analyte level. In some cases, methods, devices, and systems provided herein can automate medication delivery and use the actual dispensation times in a control algorithm determining medication deliveries.

10 Claims, 16 Drawing Sheets

(51) Int. Cl.
*A61M 5/00* (2006.01)
*G06F 19/00* (2018.01)

(52) U.S. Cl.
CPC ......... *A61M 5/172* (2013.01); *G06F 19/3468* (2013.01); *A61M 2005/16863* (2013.01); *A61M 2202/07* (2013.01); *A61M 2205/18* (2013.01); *A61M 2205/332* (2013.01); *A61M 2205/3331* (2013.01); *A61M 2205/3334* (2013.01); *A61M 2205/3569* (2013.01); *A61M 2205/3584* (2013.01); *A61M 2205/502* (2013.01); *A61M 2205/581* (2013.01); *A61M 2205/582* (2013.01); *A61M 2205/583* (2013.01); *A61M 2205/587* (2013.01); *A61M 2230/201* (2013.01)

(58) Field of Classification Search
CPC .... A61M 2205/3334; A61M 2205/581; A61M 2205/582; A61M 2205/583; A61M 2205/587; A61M 2230/201; A61M 5/16854; A61M 5/172; A61M 5/1723; G06F 19/00; G06F 19/3468
See application file for complete search history.

(56) References Cited

U.S. PATENT DOCUMENTS

| | | | |
|---|---|---|---|
| 7,892,199 B2 | 2/2011 | Mhatre et al. | |
| 7,938,797 B2 | 5/2011 | Estes et al. | |
| 8,057,436 B2 | 11/2011 | Causey et al. | |
| 8,409,142 B2 | 4/2013 | Causey et al. | |
| 8,808,230 B2 | 8/2014 | Rotstein | |
| 2009/0275887 A1* | 11/2009 | Estes ................. | A61M 5/14244 604/67 |
| 2014/0107607 A1* | 4/2014 | Estes ................... | A61M 5/1452 604/500 |

OTHER PUBLICATIONS

International Preliminary Report on Patentability in Application No. PCT/US2017/013112, dated Jul. 26, 2018, 6 pages.
Percival et al., "Closed-Loop Control and Advisory Mode Evaluation of an Artificial Pancreatic β Cell: Use of Proportional—Integral—Derivative Equivalent Model-Based Controllers," J Diabetes Sci Tech 2(4):636-644, Jul. 2008.

* cited by examiner

OCCLUSION RESOLUTION IN MEDICATION DELIVERY DEVICES, SYSTEMS, AND METHODS

CROSS-REFERENCE TO RELATED APPLICATIONS

This application claims priority to U.S. Application Ser. No. 62/278,974, filed on Jan. 14, 2016.

TECHNICAL FIELD

This document relates to systems and methods for the detection and resolution of occlusions in medication delivery devices. In some cases, the system can be adapted to use feedback from one or more sensors to detect an occlusion in a flow path from an automated medication delivery devices and, optionally, to determine how to resolve an occlusion. In some cases, methods, systems, and devices provided herein can use sensor information from occlusion detectors to determine an amount or timing of medication delivery.

BACKGROUND

Pump devices are commonly used to deliver one or more fluids to targeted individuals. In some cases, pump devices can receive feedback information from a patient to determine an amount of a fluid medication to administer to the patient. For example, an insulin infusion pump device may be used to deliver insulin to a person with diabetes (PWD) in order to control blood glucose levels and can receive information from a glucose sensor in order to determine an amount of insulin to be delivered. In use, however, occlusions can occur at either the infusion site or along the catheter (tubing) between the infusion pump and the infusion site, which can stop the delivery of medication until the occlusion is resolved. Some infusion pumps have incorporated sensors that can trigger an occlusion alarm if a threshold pressure is detected (see e.g., U.S. Pat. Nos. 8,409,142; 8,057,436; 7,892,199; 7,833,196; 7,828,528; 7,938,797; 8,808,230). Some occlusions may self-resolve overtime, after being jostled, or after sufficient pressure builds up, while other occlusions may require a user to change the infusion site or fix or change the catheter between the infusion pump and the infusion site. If an occlusion alarm triggers too early for back pressure that would have self-resolved, this can unnecessarily stress the user and potentially cause the user to experience alarm fatigue. On the other hand, significant delays in the delivery of insulin due to an occlusion can cause the PWD's blood glucose to rise, which may cause hyperglycemic events.

SUMMARY

Methods, devices, and systems provided herein are adapted to safely and effectively provide automated medication delivery (preferably, automated medication delivery (AMD)) using based at least partially upon feedback from one or more occlusion sensors and (optionally) physiological feedback from the patient. In many circumstances, the methods, devices, and systems described herein provide an improvement in differentiating between the occlusions that require user intervention and those that do not, and to gain better information regarding whether insulin is actually being delivered to the PWD. In some cases, an occlusion sensor can be a pressure sensor in a medication reservoir or along a fluid flow path from the reservoir, or a force sensor used to detect a force of a mechanism used to apply pressure to a medication reservoir. In particular embodiments, AMD the devices, systems, and methods provided herein can be adapted to deliver insulin to a person with diabetes (PWD) based on feedback from a glucose sensor and feedback from an occlusion sensor.

In particular embodiments, devices, systems, and methods provided herein can determine or estimate an amount of medication stuck-in-transit (MST) and/or an amount of active medication on board (AMOB). In one example described below, an amount of AMOB can be estimated based on the amount of medication delivered and the time the medication was delivered using a decay curve for the medication. In some implementations, the amount of AMOB can be determined based on the amounts and timing of medication delivered, but subtracting an amount of MST determined based on back pressure detected by one or more occlusion or pressure sensors, with the MST being added back to AMOB once the back pressure resolves. Also, feedback information from one or more occlusion sensors can be correlated to amounts of MST. In some cases, the medication delivered can be insulin, and an amount of Insulin On Board (IOB) can be determined based on the timing of insulin deliveries made with an insulin infusion pump, but subtracting amounts of insulin detected as being insulin stuck-in-transit (IST) when an occlusion is detected due to pressure build up and adding it back if the pressure resolves without an infusion set change. Optionally, AMD systems, devices, and methods provided herein can determine an amount of additional medication to deliver based on AMOB while ignoring the MST. In particular embodiments, AMD systems, devices, and methods provided herein can determine whether a bolus of the MST and the additional medication is safe prior to delivering the additional amount of medication. For example, an automated insulin delivery (AID) system receiving feedback from a continuous glucose monitor (CGM) and an occlusion detector can use IOB, excluding any determined IST, to determine an amount of insulin to deliver assuming that the IST will remain constant (e.g., due to a slow release of insulin that releases pressure), but also determine if a bolus of the IST would be safe for the PWD if a temporary occlusion resolves upon that delivery of insulin. For example, methods, systems, and devices provided herein can determine if the delivery of the IST insulin, in addition to the determined amount, would likely send the PWD below a safe threshold blood glucose level. If determined to be safe, the additional insulin can be administered and the occlusion sensor monitored to see if the additional insulin causes the occlusion to resolve or if pressure continues to build, which can trigger an occlusion alarm by either causing the pressure/force to increase by a determined amount or to exceed a threshold. By delivering insulin assuming that IOB does not include the IST, the systems, methods, and devices provided herein can force an occlusion alarm to trigger more quickly if the occlusion is not self-resolving by delivering an additional dosage of insulin, but ensure safety by checking to see if the delivery of all the IST would be safe. In such cases, a determination that an amount of IST is unsafe may trigger an occlusion alarm or a message to the user that the user should disconnect an infusion set to prevent a full delivery of the IST. In some cases, a replacement of an infusion set can result in the IST being cleared from the system without being delivered to the user, thus methods, devices, and systems provided herein can have an IOB calculation that excludes undelivered IST from an IOB calculation, thus improving the accuracy of a control algorithm that uses IOB to determine insulin delivery rates.

In particular embodiments, methods, devices, and systems provided herein can detect an elevated pressure in a medication reservoir or in a delivery catheter and can determine a safe amount of additional medication that can be delivered to determine if the occlusion condition will self-resolve or not. Systems, devices, and methods provided herein can also issue an occlusion alarm if the additional medication is administered and the method, device, or system determines that the occlusion condition will not self-resolve. In some cases, methods, systems, and devices may provide troubleshooting instructions to the user in response to an occlusion alarm (e.g., instructions to check a catheter for kinks, to change the infusion site, to prime the catheter, etc.). In some implementations, methods, devices, and systems provided herein can estimate an amount of medicine that remains undelivered based on data from the occlusion detector. For example, a detected pressure in a catheter can be correlated to an amount of insulin that remains undelivered, which can depend on the length, rate of delivery, lumen thickness, and material of the catheter. As described herein, methods, devices, and systems can be adapted adapted to deliver insulin to a PWD, and these systems can additionally receive blood glucose data from the PWD to determine an amount of insulin that can be delivered to the PWD safely without causing the PWD to experience hypoglycemia. For example, methods, systems, and devices provided herein may have an insulin sensitivity factor programmed in for a PWD and may have a current blood glucose level and optionally a current blood glucose trend, and may calculate a risk of a hypoglycemic event if an additional amount of insulin is administered to the user. In some implementations, methods, devices, and systems provided herein can provide users with non-disruptive tips on how to better use the system based on data from an occlusion sensor. For example, in some cases methods, systems, and devices provided herein can detect back pressure possibly due to hydrostatic pressure (i.e., pressure due to an altitude difference between the pump and an infusion site) and can provide the user with a notice that the pump should ideally be placed approximately at the same height as the infusion site.

Methods, systems, and devices provided herein can also adjust estimates of an amount of active medication remaining in a patient's body based on data from an occlusion sensor. For example, many medications have an active half-life after being administered to a patient, thus a determination or estimation of an amount of active medication in the user's body can be used to make future therapy decisions (either automatically or by the user). An occlusion condition, however, can delay when medication is actually delivered to the user. For example, pressure in a catheter can indicate that a certain volume of medication remains in the catheter, thus data from occlusion sensors can be used in methods, devices, and systems provided herein to produce a more accurate estimation of an amount of medication that remains active in a patient's body by not including medicine that remains in the catheter and/or by knowing when the medication was actually delivered to the user by tracking when the occlusion was resolved. In some cases, methods, systems, and devices provided herein can collect data regarding how an occlusion was resolved to make a determination of whether the medication was actually delivered. For example, methods, devices, and systems provided herein can use a troubleshooting tutorial to determine if that occlusion was resolved by removing the catheter from the infusion site or by replacing the infusion site, which would allow methods, systems, and devices provided herein to assume that the medication remaining in the catheter was not delivered. In some cases, methods, devices, and systems provided herein may make assumptions regarding the delivery of medication that maximize the safety of the patient. For example, if the data makes it unclear if a PWD received insulin, methods, devices, and systems provided herein may assume that that insulin was delivered in order to mitigate against the risk of a hypoglycemic event.

Methods, systems, and devices provided herein can also use pressure data or pressure proxy data (optionally from an occlusion detector) to detect possible disconnects from an infusion site. In particular embodiments, discrete pumping operations may cause a temporary pressure increase in the catheter during each pumping operation. In some cases, systems, methods, and devices provided herein can alarm if a pressure increase during a discrete pumping operation does not exceed a threshold. For example, a disconnected catheter may produce a small pressure rise. In some such situations, a larger pressure rise than normal might indicate that the infusion site may begin to occlude soon. In particular embodiments, the pressure spike profile for each discrete pumping operation may provide additional information about the infusion site (e.g., the location on the body, the age of the infusion site, whether medication is tunneling back towards the surface of the patient's skin). In some cases, methods, systems, and devices may alert the user against placing an infusion site at certain locations, about an upcoming need to change the infusion site, or to confirm that the catheter is properly secured to the infusion site.

Methods, systems, and devices provided herein can also use pressure data or pressure proxy data (optionally form an occlusion detector) to determine a relative position of the infusion site with respect to an infusion pump, which can be used to advise a user regarding an ideal relative positioning. An altitude difference between an infusion pump and an infusion site can result in hydrostatic pressure. If the pump is below the infusion site, the hydrostatic pressure increases the pressure detected in the catheter or reservoir. For example, a user sleeps in a bunkbed and places the pump on a night stand causing there to be a significant hydrostatic pressure. This hydrostatic pressure cause false occlusion alarms in systems that alarm immediately alarm immediately after any pressure is detected. Methods, devices, and systems provided herein, however, can observe detected pressures that remain approximately constant and determine that the pressure is due to a hydrostatic pressure and not an occlusion. If it is determined that a prolonged detected pressure is not an occlusion (due to an approximately steady state detected pressure), methods, devices, and systems provided herein can provide a non-disruptive tip or notice to a user explaining that an altitude difference was noticed for a prolonged period of time and/or telling the user to try to keep the pump at a height/altitude approximately the same as the infusion site. Additionally, if the infusion site is significantly below the pump and here is a particularly sensitive pressure sensor, a pressure rise during a pumping operation may not be as great as expected for the system, thus a troubleshooting evaluation questioning whether the infusion site is disconnected might also ask a user about the relative heights of the pump and infusion site.

In particular embodiments, methods, devices, and systems provided herein can automate the delivery of insulin to a person with diabetes (PWD) based on the PWD's blood glucose levels and/or occlusion detector data. In some cases, methods, devices, and systems provided herein can suspend, reduce, or increase an amount of basal insulin delivered to a PWD based on blood glucose data. Methods, devices, and systems provided herein can calculate an amount of active insulin in the PWD's body (e.g., calculate an IOB) based on deliveries of insulin to the PWD, using occlusion detector data to adjust the timing of insulin delivery based on any resolved occlusion conditions. In some implementations, an occlusion detector may require a threshold pressure in an insulin reservoir or in the infusion catheter before any back pressure will register, thus the detection of any back pressure may indicate that an amount of insulin thought to have been delivered was not delivered. Optionally, methods, devices, and systems can subtract an amount of insulin from the IOB upon an occlusion detector registering a threshold back pressure or registering any back pressure or methods, devices, and systems can trigger a delivery of a line-clearing bolus upon a determination that a first threshold occlusion condition is present and a determination that the delivery of the line-clearing bolus is safe for the PWD. For example, a safe line-clearing bolus can be based on the insulin sensitivity factor (ISF) of the PWD, the current blood glucose level of the user and optionally a blood glucose trend (e.g., from a continuous glucose monitor), an estimate of the IOB, and optionally projected blood glucose levels for the PWD based on said information. In some implementations, methods, devices, and systems provided herein can require an attempted delivery of a line-clearing bolus to determine if the occlusion condition is an occlusion that is likely to self-resolve prior to the issuance of an occlusion alarm. For example, if it is not safe to deliver the line-clearing bolus, it may indicate that the failure to deliver insulin is not yet dangerous to the PWD. In particular embodiments, an occlusion alarm threshold for an occlusion alarm may be lower than a threshold to deliver a line-clearing bolus. Methods, devices, and systems provided herein can monitor occlusion detector data during and after the delivery of a line-clearing bolus to determine if the additional insulin delivery further increases the back pressure in the insulin reservoir or infusion catheter or if it caused an occlusion condition to self-resolve. For example, if the pressure increases consistent with a full occlusion, this may trigger an occlusion alarm. In some cases, for example, a near zero change to the pressure detected after the line-clearing bolus may indicate that the detected pressure is possibly due to hydrostatic pressure, which may indicate that a disruptive alarm is not needed. Optionally, methods, devices, and systems provided herein may reduce future basal insulin deliveries to the PWD based on the delivery of the line-clearing bolus. For example, if the line-clearing bolus delivers 0.5 units of insulin, the basal insulin delivery may be delayed for a period of time during which that amount of insulin would have been delivered via the basal insulin delivery (e.g., the number of units delivered divided by the basal rate). In particular embodiments, methods, devices, and systems may only deliver line-clearing boluses when continuous blood glucose data is available and when basal insulin therapy is being actively automated.

Some embodiments of an infusion pump system may include one or more sensors for detecting a fluid pressure within an infusate flow pathway. The detected fluid pressures can be advantageously used by the infusion pump system in various ways. For example, in some embodiments, the detected fluid pressure can indicate when an occlusion exists in the infusate fluid pathway, and an alarm can alert the user to the presence of such an occlusion. In some embodiments, the detected fluid pressure can be used to determine an accurate time and amount of infusate delivered to the user. Such information can be used by the infusion pump system, for example, to accurately predict the user's future blood glucose levels. In some embodiments, the detected fluid pressure can be used to confirm whether a dispensation of infusate was actually delivered into the user's body (e.g., the user's vasculature).

Some or all of the embodiments described herein may provide one or more of the following advantages. First, the infusion pump system may include a pressure detection configuration that accurately detects occlusions in the infusate flow path extending from the pump device to the user. As such, the occlusion sensor feature can provide a notice (e.g., an alarm, an alert, etc.) to the user if he or she is receiving no dosage or a lower than desired dosage of infusate due to an occlusion in the infusate flow path. Such an occlusion may occur, for example, when the infusate fluid flow line (e.g., a cannula, infusion set tubing, or the like) is kinked.

Second, some embodiments of the infusion pump system may include a pressure detection configuration that can be used to determine an accurate time and an accurate amount of infusate actually delivered to the user. In some implementations, an occlusion in the infusate pathway is a transient occlusion. That is, for example, an occlusion may exist at the time of an infusate delivery, but later the occlusion may become fully or partially eliminated. In such a case, a desired dispensation of an amount of infusate may initially be either fully or partially reduced, and at a time thereafter the residual pressurized infusate in the pathway may be subsequently delivered to the user when the occlusion is eliminated. The pressure detection configuration can thereby be used to detect the actual amounts and the actual times at which both the initial and the subsequent infusate deliveries are made. Such information can be advantageously used by the infusion pump system for various purposes. For example, such information can be used to accurately predict the user's future blood glucose levels (e.g., when insulin is the infusate), which can be used in a control algorithm used to automate infusate delivery.

Third, some embodiments of the infusion pump system may include an analyte sensor. In some cases, the analyte can be used to determine an alarm threshold for triggering an occlusion alarm. For example, when insulin is the infusate, a rising blood glucose level can indicate the possibility of a new occlusion, thus a rising blood glucose trend may indicate a higher probability of an occlusion, thus an alarm threshold can be lowered so that an occlusion alarm is triggered sooner. If a PWD's blood glucose level is steady at a target level or within a target range, however, it may not be necessary to trigger an occlusion alarm as quickly if the occlusion may self-resolve. Optionally, rather than merely changing the alarm threshold for an occlusion alarm, analyte sensor data can be used to determine if an additional administration of infusate is safe. For example, if insulin is the infusate and the user is a PWD, then analyte sensor data can be used to determine if the administration of an additional dose of insulin is safe for the PWD based on the PWD's insulin sensitivity factor (ISF) and an amount of insulin stuck-in-transit (IST). For example, if an insulin pump is determined to have a back pressure corresponding to 0.5 units of IST, that can be used to determine if that IST plus an additional administration of 0.2 units is likely to send the user into a hypoglycemic condition. If it is determined to be safe, it can be delivered to see if the pressure continues to increase in a way consistent with a non-resolving occlusion. In some cases, the additional administration can be designed to send the back pressure to an amount above an occlusion alarm threshold if the additional administration does not cause the occlusion to resolve. In particular embodiments, methods, systems, and devices provided herein can evaluate a pressure increase after the additional administration to evaluate if the increase is consistent with a non-self-resolving occlusion. In some implementations, data from an analyte sensor can be used in the automation of infusate delivery, but the pressure sensor can be used to stop the automatic delivery of extra infusate above a baseline amount when an occlusion is suspected. For example, when insulin is the infusate, data from a continuous glucose monitor (CGM) for a PWD can be used to stop insulin delivery, methods, devices, and systems provided herein that can deliver insulin at a preprogrammed basal rate, at one or more larger rates, and optionally at one or more lower rates (which can be a rate of zero). In some cases, such methods, devices, and systems can prevent the delivery of the one or more larger rates of insulin delivery when a pressure sensor indicates a possible occlusion or a significant amount of IST, even before an occlusion alarm is triggered, which can prevent an amount of IST from becoming too large prior to an occlusion self-resolving. In these cases, additional insulin deliveries can be used during this period of time to test whether the occlusion condition is likely to self-resolve to determine whether to sound an occlusion alarm.

Third, some embodiments of the infusion pump system may include a pressure detection configuration that can be used to indicate whether a dispensation of infusate was actually delivered into the user's body (e.g., into the user's vasculature). For example, when an infusate is being dispensed into the user's body, the pressure in the infusate pathway will expectantly increase because of back pressure associated with the user's body. If, however, the infusate fluid flow line is not coupled to the user at the time of the infusate dispensation, no such back pressure will be present, and the pressure in the infusate pathway will therefore be less than expected. When a lower than expected infusate pathway pressure is detected during an infusate dispensation, the infusion pump system may ascertain that no infusate was delivered to the user because the infusate fluid flow line was not coupled to the user. In some cases, appropriate countermeasures can then be initiated by the infusion pump system, such as an alert or alarm to the user to prompt the user to properly install the infusate fluid flow line.

Fourth, some embodiments of the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

Thus, the embodiments described herein provide the benefit of a medicine delivery system that can better differentiate between occlusions that require user intervention and those that do not, and allowing users to gain better information regarding whether insulin is actually being delivered to the PWD.

DETAILED DESCRIPTION

Medication delivery methods, devices, and systems provided herein can use occlusion sensor data to more quickly and/or more accurately identify occlusions, to improve the automation of medication delivery, use analyte data to improve the accuracy and timing of occlusion alarms, and can detect disconnected infusion sets. In some cases, methods, devices, and systems provided herein can use occlusion sensor data to distinguish between AMOB and medication stuck-in-transit (MST), which can be used to improve the automation of medication delivery. In particular embodiments, the medication delivery methods, devices, and systems, can be insulin delivery methods, devices, and systems. In some cases, methods, devices, and systems provided herein can be Automated Insulin Delivery (AID) methods, devices, and systems.

Figure 1:
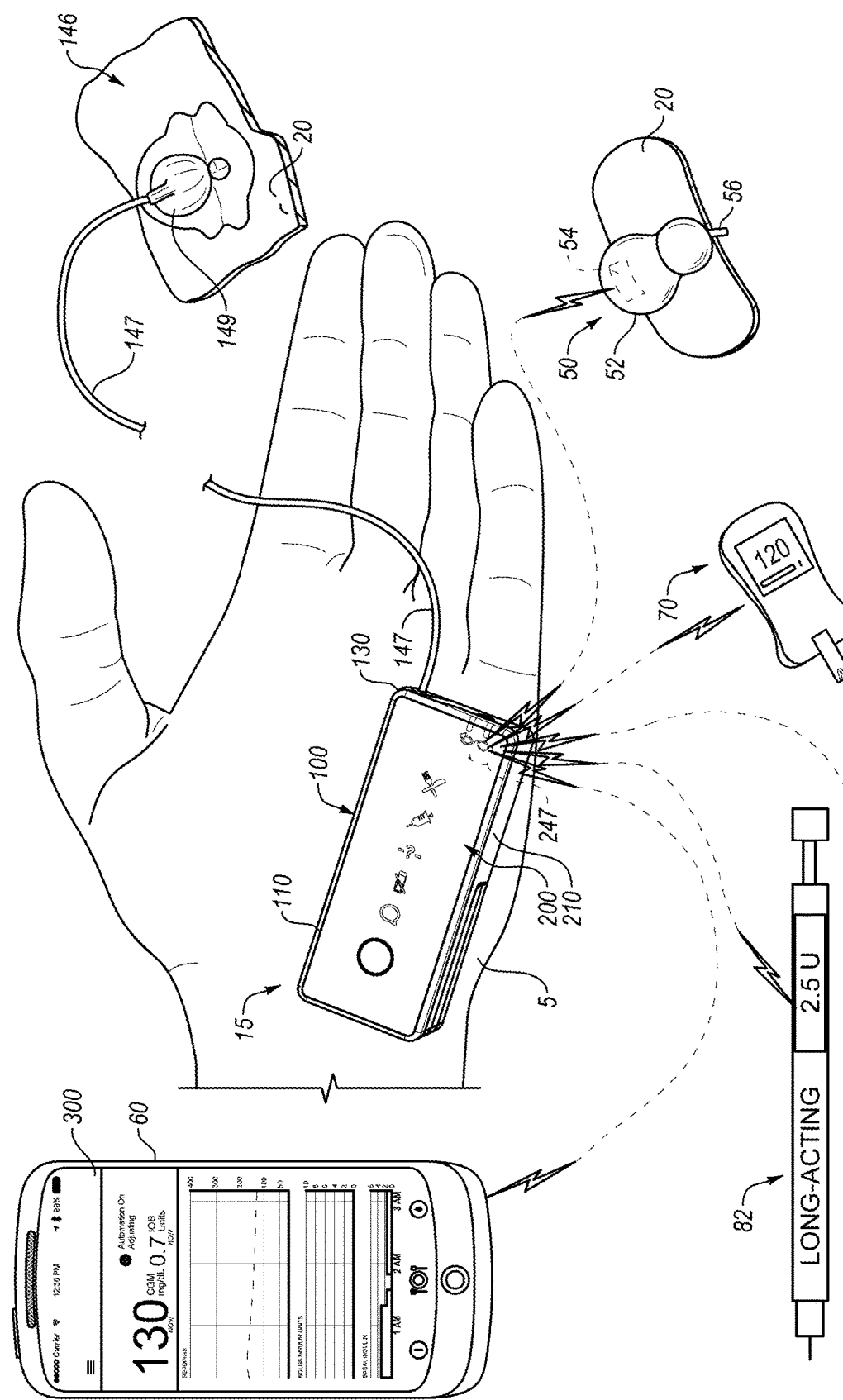
FIG. 1 is an exploded perspective view of an example diabetes management system.
Figure 2A:
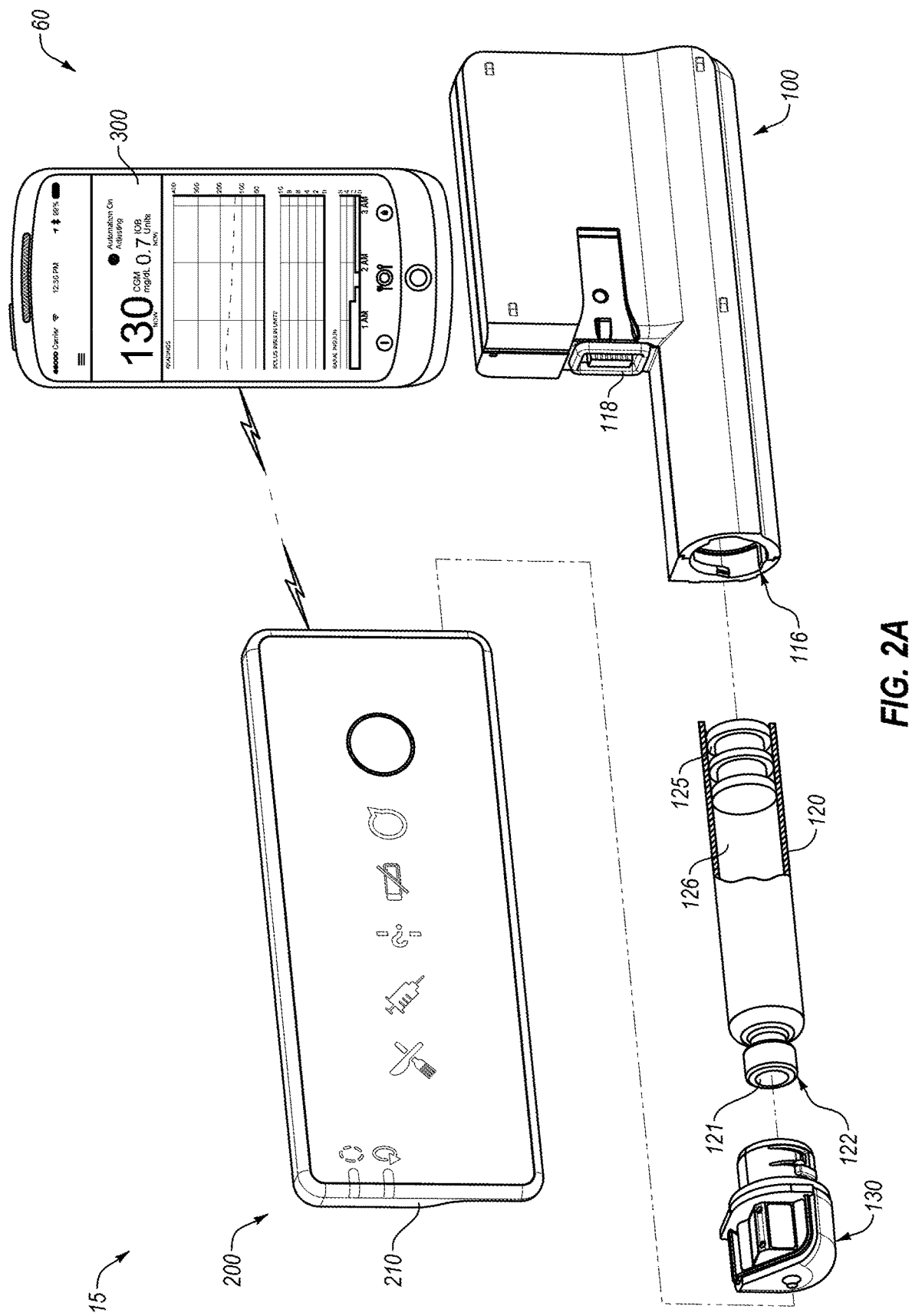
FIG. 2A depicts details about an exemplary insulin pump.
Figure 2B:
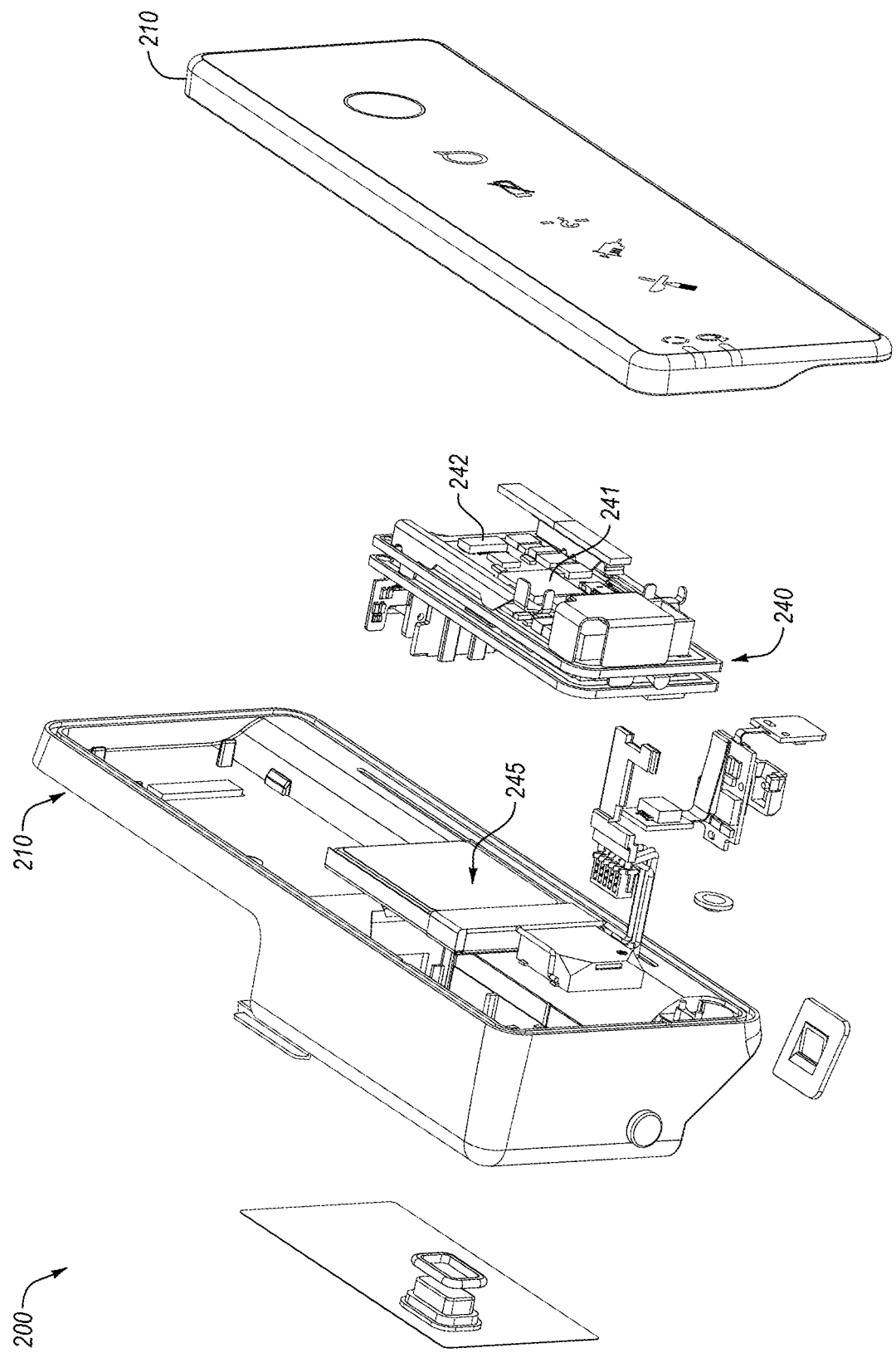
FIG. 2B depicts details about an exemplary insulin pump controller of the exemplary insulin pump of FIG. 2A.

FIG. 1 provides an example of an infusion pump system 10 (also referred to herein as a diabetes management system (DMS)) that includes an infusion pump assembly 15, a mobile computing device 60, a continuous glucose monitor 50, and a blood glucose monitor 70. FIG. 2A depicts the infusion pump system 10 in greater detail. FIG. 2B depicts the details of an exemplary pump controller 200, which can be used with infusion pump system 10. While infusion pump system 10 is referred to herein as a DMS system, it should be understood that infusion pump system 10 is not limited to such a context. In some cases, the systems and methods may be adapted for use with additional chronic diseases or conditions, for example, unresponsive infections, cancer, cancer-related pain, chronic pain, gastrointestinal diseases or disorders, congestive heart failure, hemophilia, immune deficiencies, multiple sclerosis, and rheumatoid arthritis. Similarly, while the infusate delivered from infusion pump assembly 15 is referred to herein as insulin, it should be understood that other types of infusate may also be delivered using infusion pump assembly 15. The DMS 10 and methods provided herein may be used and performed, respectively, by a user, for example, a type 1 or 2 diabetes patient or a caregiver of a diabetes patient.

Additional details about DMS 10 is discussed below in reference to FIGS. 1, 2A, and 2B. FIG. 3A-6C depict the particular occlusion sensor used in DMS 10, and illustrate how it can work. FIG. 7 is a flowchart depicting how an occlusion can be detected using the occlusion sensor of FIGS. 3A-6C. These are discussed in greater detail below. Moreover, details about the occlusion sensor is additionally described in U.S. Pat. No. 8,808,230, which is hereby incorporated by reference. Other occlusion sensing arrangements are also described in U.S. Pat. Nos. 8,790,294; 7,828,528; and 8,852,141, which are hereby incorporated by reference.

Figure 9A:
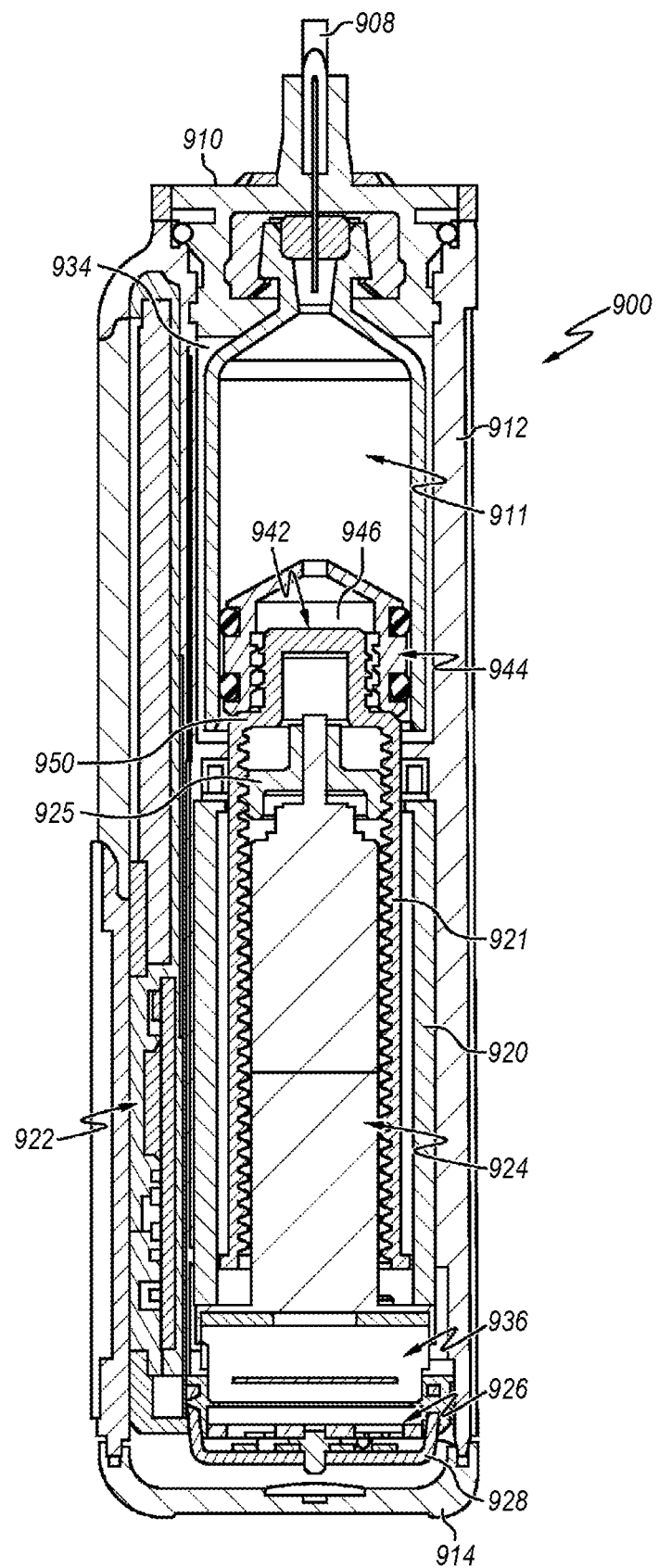
FIGS. 9A and 9B illustrate an alternative example of an insulin pump.
Figure 9B:
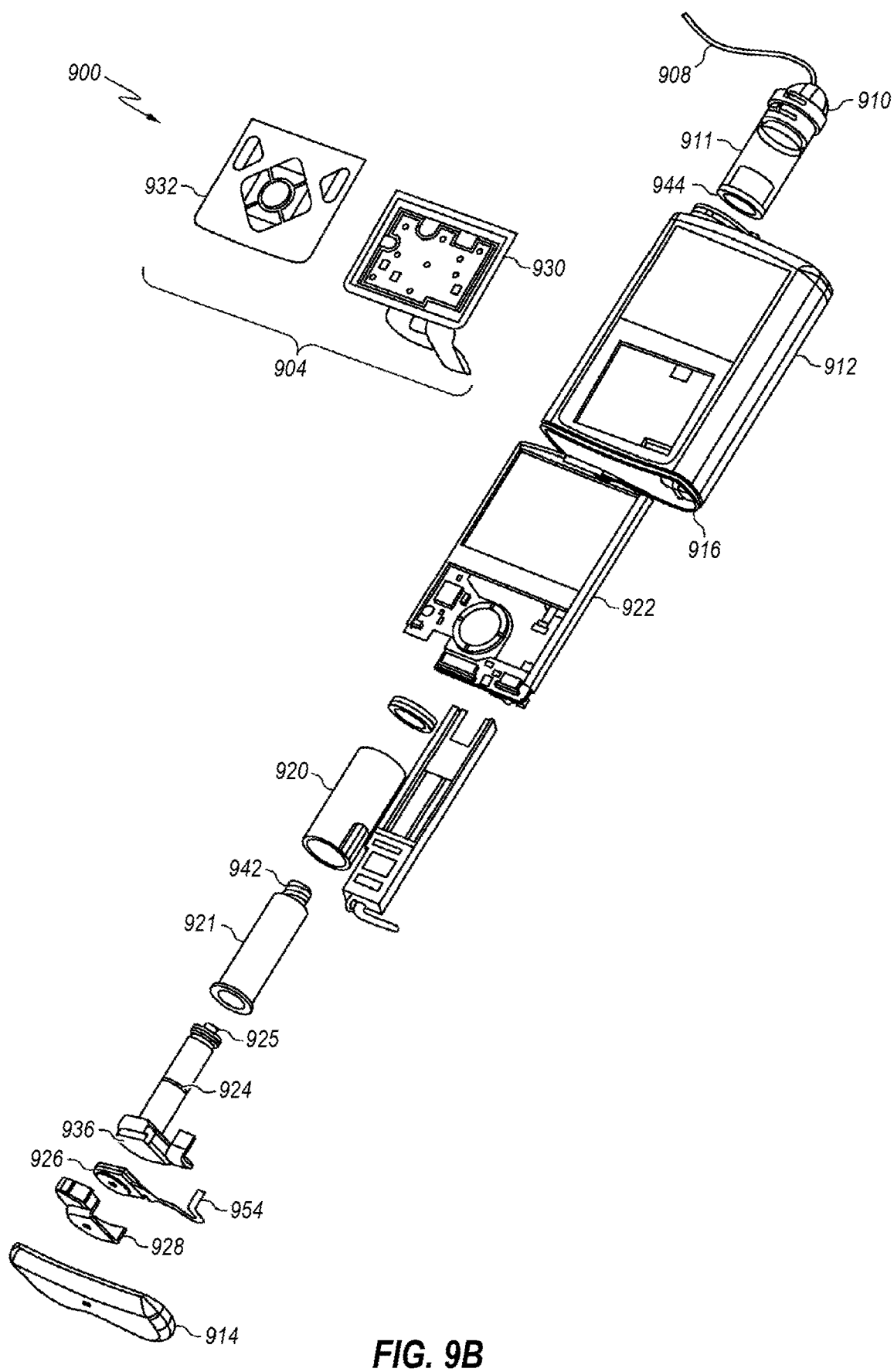

FIGS. 9A and 9B depict an alternative infusion pump 900, which can include a force sensor as part of a drive system to detect possible occlusion conditions. In some cases, infusion pump 900 can be incorporated into DMS 10 in place of infusion pump assembly 15, or may be used in place of both infusion pump assembly 15 and mobile computing device 60. As described below, data from the force sensor can be used to detect possible occlusion conditions and to determine when to trigger an occlusion alarm. Additionally, in particular embodiments, data from the force sensor can be used to trigger an additional dosage of infusate (if that additional dosage is determined to be safe) to either cause the possible occlusion condition to resolve or trigger conditions that trigger an occlusion alarm. In some cases, a threshold for triggering the alarm using force sensor data can be variable based on data from an analyte monitor. In some cases, data from a force sensor can be sensitive enough to detect if an infusion set is disconnected.

Figure 8A:
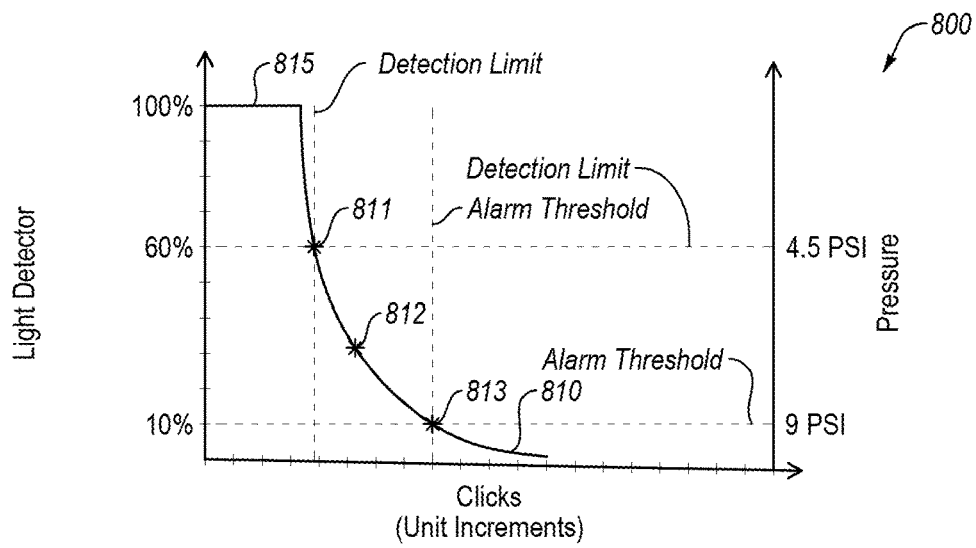
FIG. 8A is a graphical representation illustrating a relationship between data from an occlusion detector, pressure, and units of medication in the line.
Figure 8B:
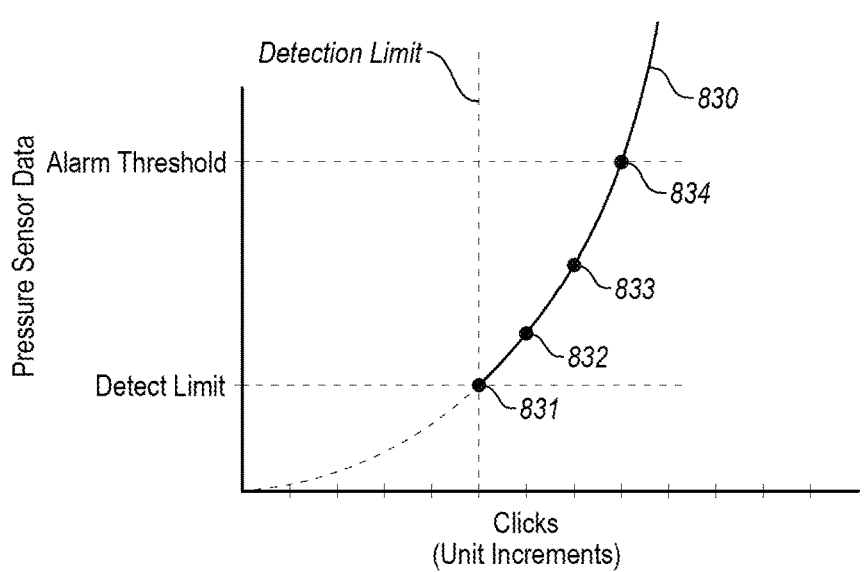
FIG. 8B illustrates a possible relationship between a pressure sensor and units of medication in the line.
Figure 8C:
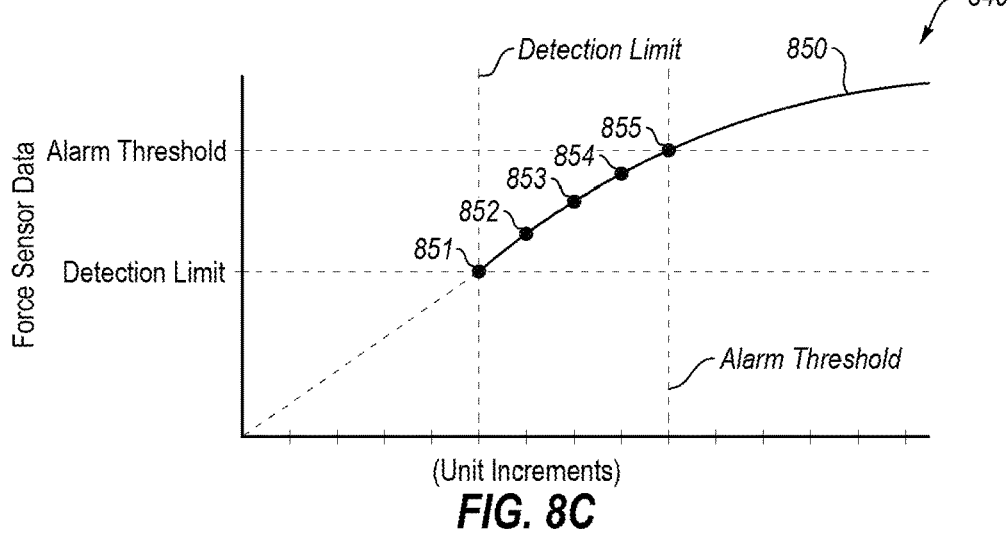
FIG. 8C illustrates a possible relationship between a force sensor and units of medication in the line.

FIG. 8A illustrates how occlusion sensor data from a sensor described below in relation to FIGS. 3A-6C can be correlated to a pressure. FIG. 8B graphically illustrates how discrete dosage amounts can increase the pressure detected when a pump is in an occluded condition. FIG. 8C graphically illustrates how discrete dosage amounts can increase the force detected with a pump is in an occluded condition. Occlusion sensors and infusion pumps can be tested to determine the behavior of the occlusion sensor/infusion pump when infusate is pumped into the catheter when the catheter is in a fully occluded condition (e.g., by clamping an end of an infusion catheter while pumping infusate). FIG. 8A is specific for an occlusion sensor described below in regards to FIGS. 3A-6C, but can be applicable to other occlusion sensors, such as force sensors. FIG. 8B generically depicts an expected change in data from a pressure sensor in response to a fully occluded condition as additional units of medication are pumped. FIG. 8C depicts an expected change in data from a force sensor in response to a fully occluded condition as additional units of medication are pumped. These graphs are illustrative, and each infusion pump/occlusion detector arrangement may have different curves and different detection limits.

Figure 10:
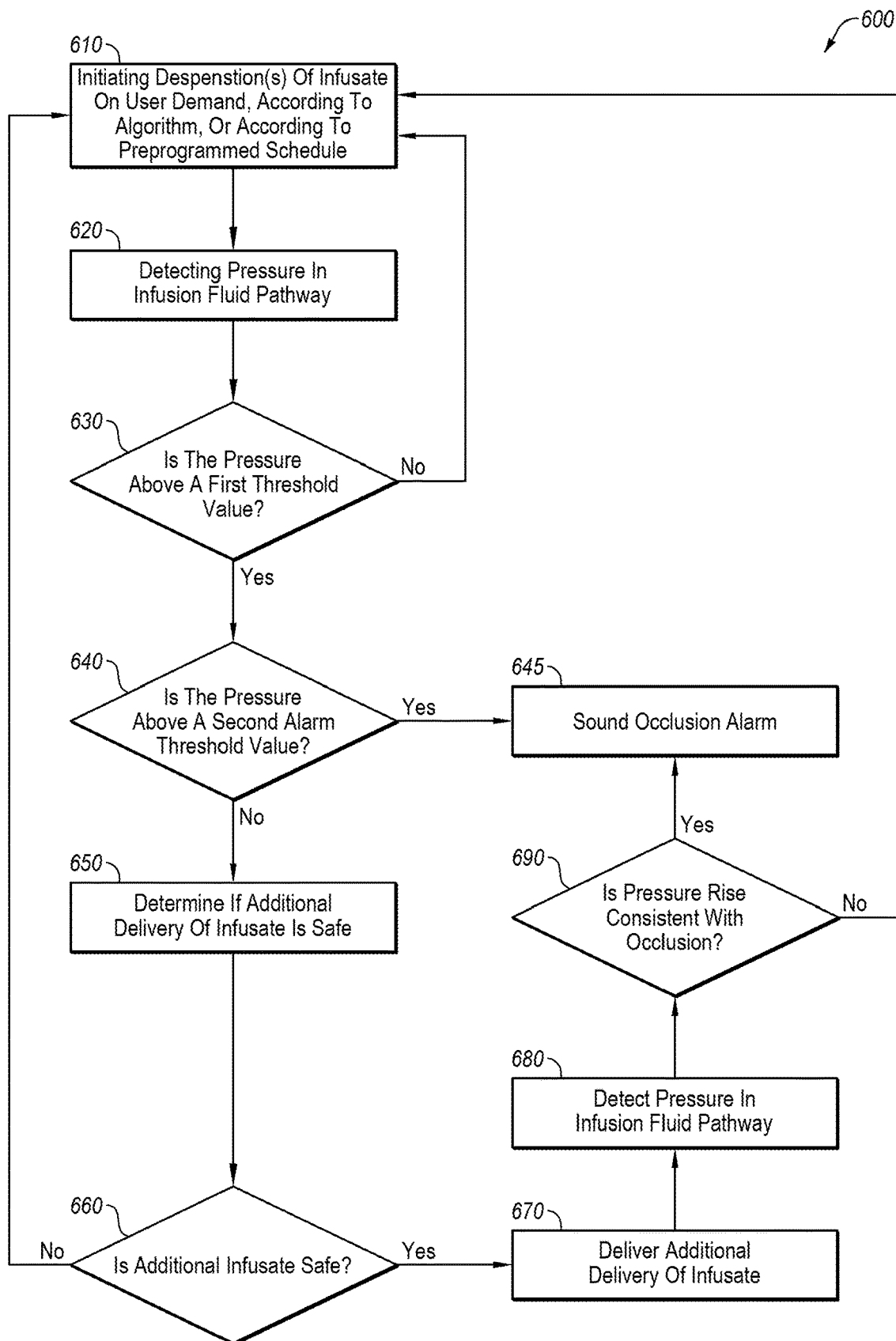
FIG. 10 is a flowchart of an example method for triggering an occlusion alarm.
Figure 11:
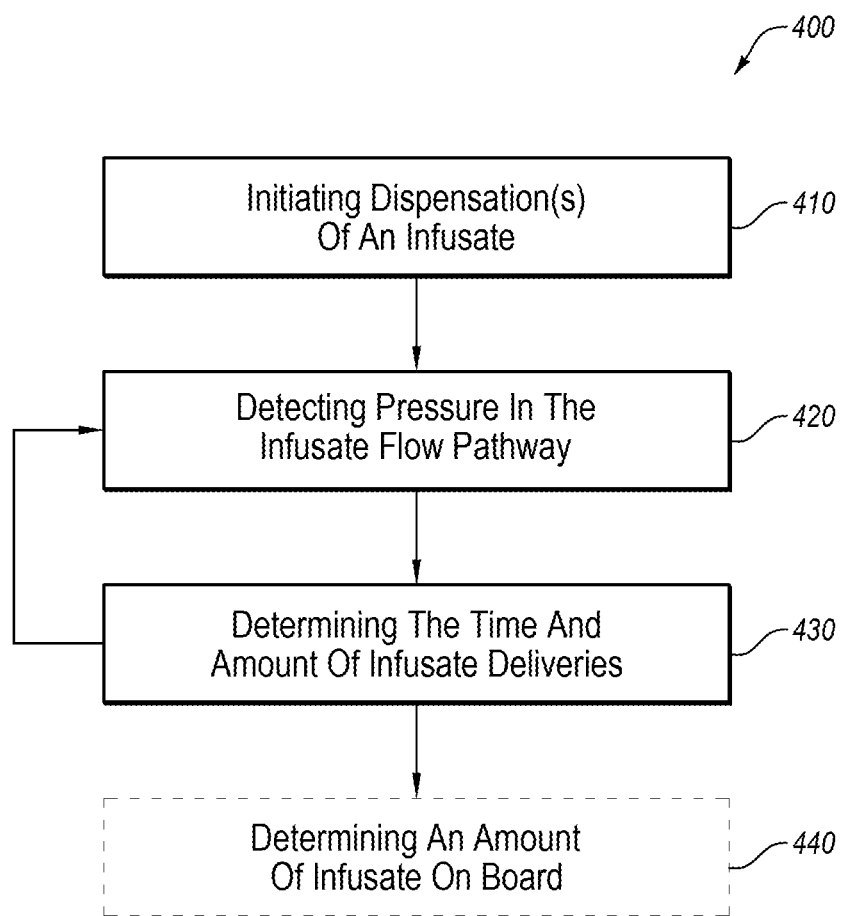
FIG. 11 is a flowchart of an example method for determining an amount of infusate on board.
Figure 12:
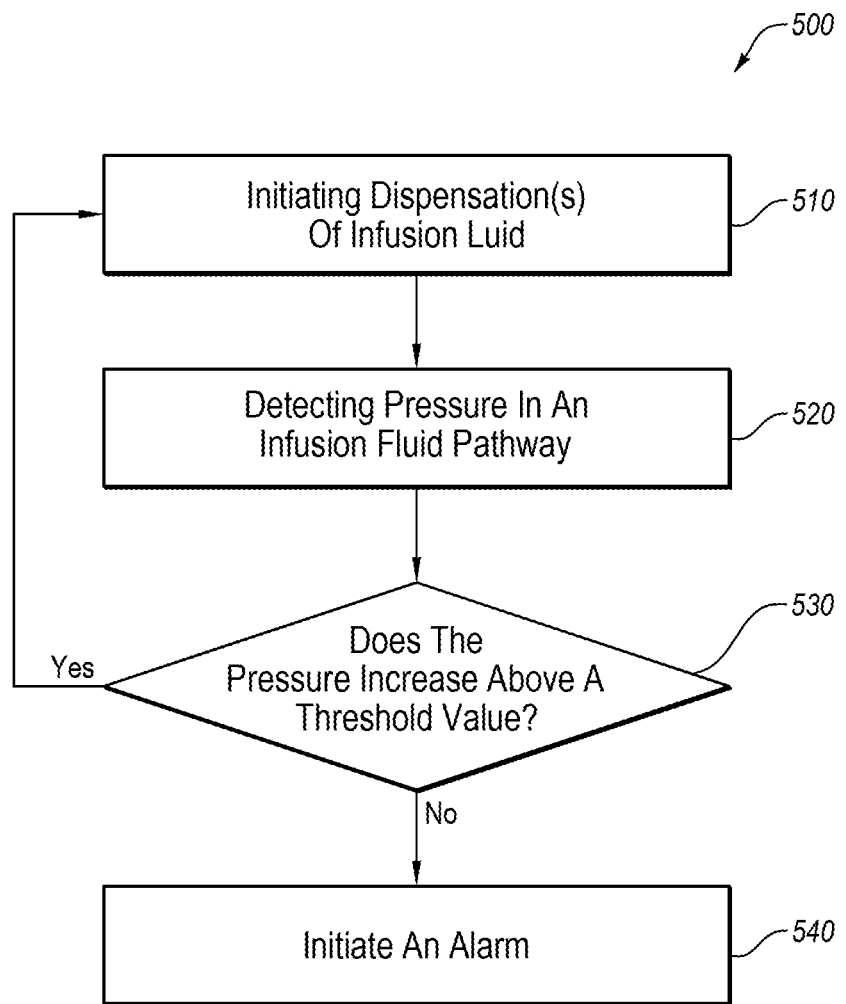
FIG. 12 is a flowchart of an example method for determining if an infusion set is disconnected.

FIG. 10 is a flowchart illustrating an exemplary method for issuing occlusion alarms or additional dosages of infusate. FIG. 11 is a flowchart illustrating an exemplary method for determining when infusate is actually delivered and optionally determining an amount of infusate on board (or active medication on board (AMOB)). FIG. 12 is a flowchart illustrating an exemplary method of determining issuing an occlusion alarm.

Methods, systems, and devices provided herein can use non-binary data from an occlusion sensor, which can be a pressure sensor or a force sensor, to more quickly identify occlusion condition in an infusion pump that require user intervention, to minimize alarms issued for self-resolving occlusion conditions, and to optionally trigger administrations of medication designed to safely test whether an non-self-resolving occlusion condition exists. Additionally, methods, systems, and devices provided herein can use non-binary data from an occlusion detector to improve the automation of medication delivery by having more accurate information about an amount of active medication on board (AMOB) by knowing an amount of medication stuck-in-transit (MST).

Determining when Medication has been Delivered

Methods, devices, and systems provided herein can use non-binary occlusion detector data to determine an amount of infusate on board or active medication on board (AMOB) by determining an amount of medication stuck-in-transit (MST). In some cases, the medication can be insulin, and methods, devices, and systems provided herein can determine an amount of Insulin-on-Board (IOB) or some other calculation of active insulin by determining an amount of Insulin Stuck-in-transit (IST). In describing these concepts, the description below references the charts of FIGS. 8A-8C to help illustrate the concepts.

Medications such as insulin typically have activity profiles which differ depending on the specific medication, and can depend on how it is delivered, the specific biochemistry of the patient, and other factors. AMOB is an estimation of how much active medication remains in the patient, and can be used to determine whether an additional administration of medication is safe and/or recommended. For example, IOB is a calculation of an amount of active insulin remaining in a person with diabetes (PWD), and can be used by the PWD to determine if the PWD should administer an additional bolus. In some cases, automated insulin delivery systems can monitor data from a glucose monitor and use that data along with a calculation of IOB to determine a subsequent insulin dosage (e.g., a bolus or a basal adjustment). Because an estimation of AMOB requires knowledge of when the medication was delivered, better data on when medication was delivered can produce more accurate estimations of an amount of AMOB. Accordingly, data from an occlusion detector can be used to determine an amount of MST.

Referring to FIG. 8A, data from a light detector in an occlusion detector can be correlated to a number of units of medication delivered for that particular infusion device, producing a chart 800. Accordingly, once the occlusion detector detects anything beyond the detection limit at 811, which corresponds to about 4 unit increments, methods, devices, and systems provided herein can determine that about 4 unit increments of medication are stuck-in-transit, thus 4 unit increments can be subtracted from the AMOB. If the pressure continues to increase such that the light detector only detects about 30% light, methods, systems, and devices provided herein can determine that about 5 unit increments of medication are stuck-in-transit by correlating point 812 along curve 810, thus avoiding adding that medication to the AMOB. If the pressure continues to increase such that an alarm threshold is met, such as an amount of light detected being less than 10% as shown, then an occlusion alarm might sound, which can trigger the user to replace the infusion set. If an infusion set is replaced, methods, systems, and devices can avoid adding the MST to the AMOB, thus improving the administration of medication after the infusion set is replaced. In some cases, an occlusion condition may self-resolve prior to reaching the alarm threshold, such that methods, systems, and devices provided herein can add the MST, or a portion thereof, to the AMOB and/or determine the timing of the MST admiration. As shown in FIG. 8A, some occlusion sensors might not be configured to detect any data when a pressure is below a detection limit, thus the light detector does not detect the occlusion for the first 3 clicks, thus below the detection limit, the curve is flat at 815. In some cases, occlusion detectors can be more sensitive and detect small pressure increases, thus reducing or eliminating flat section 815 for their detection curve.

Referring to FIG. 8B, data can be collected from a generic pressure sensor, which can be a pressure sensor that uses reflected light or any other type of pressure sensor. This collected pressure date is used to determine a pressure curve for a particular infusion pump such as shown as chart 820. Again, this chart can be developed by testing an infusion pump in a fully occluded condition. Similar to chart 800, chart 820 can have a detection limit and an alarm threshold, and can correlate a plurality of points 831-834 along curve 830 so that a detected pressure corresponds to a number of unit increments of medication stuck-in-transit (MST), which can similarly be used to produce a better determination of AMOB.

Referring to FIG. 8C, data can be collected from a force sensor, such as that described below in reference to FIGS. 9A and 9B. This collected force sensor data is used to determine a force curve for a particular infusion pump such as shown as chart 840. Again, this chart can be developed by testing an infusion pump in a fully occluded condition. Similar to charts 800 and 820, chart 840 can have a detection limit and an alarm threshold, and can correlate a plurality of points 851-855 along curve 850 so that a detected force corresponds to a number of unit increments of medication stuck-in-transit (MST), which can similarly be used to produce a better determination of AMOB.

In some cases, these curves can depend on the material(s) and/or length(s) of the particular infusion catheter or infusion sets used, thus in some cases, methods, devices, and systems provided herein can use data about a particular infusion set or infusion catheter being used to make adjustments to the correlation between occlusion sensor data and a determined amount of MST. The detection limit of each sensor can be due to compliance in the sensor design.

Referring to FIG. 11, an example method 400 can be used for operating an infusion pump system configured with an infusate pressure detection system (as described above) in regards to FIGS. 8A-8C. Such an infusion pump system may include one or more sensors for detecting a fluid pressure within the infusate flow pathway (e.g., within an infusion set). As discussed above, data from any occlusion sensor, including a light detecting occlusion sensor or a force sensor, can be correlated to a pressure.

Method 400 begins at step 410 with the initiation of a dispensation of infusion fluid. For example, in some embodiments, step 410 can comprise an activation (by an infusion pump controller) of a drive system of the infusion pump with the purpose of dispensing a particular amount of infusate to the user of the infusion pump. In some examples, a particular number of units of infusate (e.g., the medication, which can be insulin) may be intended to be delivered to the user by virtue of the activation of the infusion pump drive system. The drive system of the infusion pump can be designed to dispense an accurately controlled amount of infusate. The controller of the infusion pump can initiate and control the activation of the pump drive system so that a targeted (intended) amount of infusate is dispensed as a result of the activation (assuming there are no unintended occlusions within the infusate flow path).

At step 420, the fluid pressure within the infusate flow pathway is detected by the controller of the infusion pump. The pressure detection may be performed using various devices and techniques, as described herein. In some cases, pressure signals are collected on a periodic basis (e.g., once per second, once per 5 seconds, once per 10 seconds, once per 20 seconds, once per 30 seconds, once per 45 seconds, once per minute, less frequently than once per minute, and the like, and within ranges thereof). In some cases, pressure signals may be collected multiple times during the actuation of the mechanical delivery to characterize the pressure profile during the delivery. Signals from pressure detectors can be sent to and received by a control circuitry of the infusion pump. The control circuitry can store the detected pressure signals in memory for analysis and processing. In some cases, the control circuitry stores a timestamp in association with the detected pressure signals. Hence, a time-based pressure profile of the fluid pressure within the infusate flow pathway can be created by the control circuitry. Such data can be further analyzed and processed by the control circuitry. For example, the data can be compared to threshold values, the data can be analyzed to identify times when changes in pressure occurred, the data can be analyzed to identify trends, and the like.

At step 430, the controller of the infusion pump determines the time and amount of infusate deliveries. The controller can use the pressure data collected in step 420 to perform step 430. As described further in the following example, using the pressure data collected in step 420 can, in some cases, enhance the accuracy of the determination of the time and amount of infusate deliveries (as compared to merely relying on the initiation of intended infusate deliveries from step 410). For example, an amount of MST can be determined based on a detected pressure or a pressure estimate based on a force sensor or other type of occlusion sensor, and the amount of MST can be excluded from a calculation of AMOB. Such accuracy enhancements can provide user advantages such as better management of blood glucose levels.

For example, the controller in step 430 can identify an occlusion in the infusate flow pathway by measuring and analyzing the fluid pressure within the infusate flow pathway during such a dispensation. Additionally, fluid pressure within the infusate pathway can be due to hydrostatic pressure. Infusate dispensations (timing and amount) that are affected by partial occlusions, transient occlusions, and/or hydrostatic pressure can be identified by the controller by measuring and analyzing the fluid pressure within the infusate flow pathway after the pump drive mechanism is activated for such a dispensation. For example, in some cases a transient occlusion can reside in the infusate flow pathway. When a transient occlusion resides in the infusate flow pathway, an intended dispensation will be initially partially or fully prevented from actually reaching the user, but later (after the occlusion is obviated) the intended dispensation will be actually delivered. By measuring and analyzing the fluid pressure within the infusate flow pathway during such a dispensation, the infusion pump control circuitry can identify the amount(s) and time(s) when the infusate was actually delivered to the user. Similarly, an altitude difference between the infusion pump and infusion site can result in back pressure and result in MST until the height difference is eliminated. Such information about MST can be advantageous, for example, to calculate the insulin-on-board for a user and in algorithms that use insulin-on-board as a parameter for managing the user's blood glucose level. Insulin-on-board is a term of art generally describing an amount of insulin that has been dosed to the user but whose blood glucose lowering effect has not yet occurred due to delayed action in the pharmacodynamics of subcutaneously infused insulin.

When a transient occlusion resides in the infusate flow pathway, a dispensation will cause the infusate pressure to rise and remain above the steady-state level for period of time that is longer than normal (here "normal" refers to the scenario with no unintended occlusions in the infusate flow pathway). Subsequently, at some time thereafter, the infusate pressure will reduce to the normal the steady-state level (indicating that the entire amount of infusate has then actually been delivered). By measuring and analyzing the fluid pressure within the infusate flow pathway during such a dispensation, the control circuitry can identify such an occurrence and can ascertain the time(s) when the infusate was actually delivered.

In some cases, the lack of temporary back pressure during a pumping operation may indicate that an infusion set is disconnected and that the user is not receiving medication, or that the infusion site is much lower in altitude than the infusion pump. Typically, a dispensation of infusate will result in a short-lived rise in the fluid pressure within the infusate flow pathway. The rise will occur while the infusate is flowing from the infusion pump to the user. During such flows, the pressure will rise from a steady-state pressure level and then return to approximately the same steady-state pressure level when the dispensation has been completed. By measuring and analyzing the fluid pressure within the infusate flow pathway during such a dispensation, if there is a pressure sensor sensitive enough to detect this temporary back pressure during a pumping operation, the infusion pump control circuitry can confirm that the intended amount of infusate was actually delivered to the user at the intended time. By extension, the control circuitry can also identify deviations from such intended infusate dispensations (timing and amount) by measuring and analyzing the fluid pressure within the infusate flow pathway during such a dispensation, and query the user to check that the infusion site is properly installed and/or the relative heights of the infusion pump and the infusion site.

A repetitious loop can exist between steps 430 and 420. That is, pressure detection and pressure data analysis can be repeated again and again to ascertain accurate knowledge (by the infusion pump controller) of the timing and amounts of the actual deliveries of the infusate to the user.

In optional step 440, the controller can determine an amount of active medication on board (AMOB), which can also be referred to as infusate on board, using the information determined in previous step 430. This step is just one example of how the information determined in previous step 430 can be used in an advantageous manner. The effectiveness of blood glucose management by a closed-loop infusion pump system (and/or an open-loop system) is negatively affected when intended dispensations of insulin are not actually delivered to the user. Such a situation is exacerbated when the device or person(s) making decisions about the times and amounts of future dispensations of insulin is/are unaware of the discrepancies between the intended and actual dispensations. Hence, method 400 provides awareness of such discrepancies, and the awareness can be put to practical use here in step 440. For example, in the case of a transient occlusion as described above, some or all of the insulin dispensation was delayed (i.e., some or all of the insulin dispensation occurred later than at the intended time). As such, the user's blood glucose level may be above a targeted level for longer than expected (because the delayed insulin has not yet been metabolized). If the fact that the dispensation was merely delayed as a result of a transient occlusion is known by the decision-maker (either device or person(s)), the decision-maker will not "over-react" by initiating an unneeded or excessive dispensation to bring the blood glucose level down. Instead, the decision-maker will understand that the user has the insulin-on-board as needed to perhaps eventually bring the blood glucose level down to the targeted level.

Detecting Disconnected Infusion Set

In some cases, certain occlusion detectors with detection thresholds that permit the detection of transient pressure increases during the pumping of infusate or medication can be used to determine if an infusion set is disconnected to trigger an alarm. Referring to FIG. 12, an example method 500 can be used for operating an infusion pump system configured with an infusate pressure detection system (as described above). Such an infusion pump system may include one or more sensors for detecting a fluid pressure within the infusate flow pathway (e.g., within an infusion set).

Method 500 can be used to detect whether a dispensation of infusate was actually delivered into the user's body (e.g., subcutaneously). For example, when an infusate dispensation is being made into the user's body, the pressure in the infusate pathway will expectantly increase because of back pressure associated with the user's body. If, however, the infusate fluid flow line is not coupled to the user at the time of the infusate dispensation, no such back pressure will be present, and the pressure in the infusate pathway will therefore be less than expected. When a lower than expected infusate pathway pressure is detected during an infusate dispensation, the infusion pump system may ascertain that no infusate was delivered to the user because the infusate fluid flow line was not coupled to the user. In some cases, appropriate countermeasures can then be initiated by the infusion pump system, such as an alert or alarm to the user to prompt the user to properly install the infusate fluid flow line.

Method 500 begins at step 510 with the initiation of a dispensation of infusion fluid. For example, in some embodiments, step 510 can comprise an activation (by an infusion pump controller) of a drive system of the infusion pump with the purpose of dispensing a particular amount of infusate to the user of the infusion pump. In some examples, a particular number of units of insulin may be intended to be delivered to the user by virtue of the activation of the infusion pump drive system. The drive system of the infusion pump can be designed to dispense an accurately controlled amount of infusate. The controller of the infusion pump can initiate and control the activation of the pump drive system so that a targeted (intended) amount of infusate is dispensed as a result of the activation (assuming there are no unintended occlusions within the infusate flow path).

At step 520, the fluid pressure within the infusate flow pathway is detected by the controller of the infusion pump. The pressure detection may be performed using various devices and techniques, as described above. In some cases, pressure signals are collected on a periodic basis (e.g., between every discrete dispensing operation, once per second, once per 5 seconds, once per 10 seconds, once per 20 seconds, once per 30 seconds, once per 45 seconds, once per minute, less frequently than once per minute, and the like, and within ranges thereof). In some cases, pressure signals may be collected multiple times during the actuation of the mechanical delivery to characterize the pressure profile during the delivery. Signals from pressure detectors can be sent to and received by a control circuitry of the infusion pump. The control circuitry can store the detected pressure signals in memory for analysis and processing. In some cases, the control circuitry stores a timestamp in association with the detected pressure signals. Hence, a time-based pressure profile of the fluid pressure within the infusate flow pathway can be created by the control circuitry. Such data can be further analyzed and processed by the control circuitry. For example, the data can be compared to threshold values, the data can be analyzed to identify times when changes in pressure occurred, the data can be analyzed to identify trends, and the like.

When an infusion set is properly coupled to the user, a dispensation of infusate will result in a short-lived rise in the fluid pressure within the infusate flow pathway. The pressure rise will result because of back-pressure from the user's body (e.g., vasculature), and occur while the infusate is flowing from the infusion pump to the user. During such flows, the pressure will rise from a steady-state pressure level and then return to approximately the same steady-state pressure level when the dispensation has been completed. By measuring and analyzing the fluid pressure within the infusate flow pathway during such a dispensation, the infusion pump control circuitry can confirm that the infusion set is coupled to the patient. By extension, the control circuitry can also identify deviations from such intended infusate dispensations by measuring and analyzing the fluid pressure within the infusate flow pathway during such a dispensation. The analysis of the pressure level during the actuation of the delivery may include characterizing any number of metrics such as the shape of the pressure profile during delivery, the maximum pressure level during delivery, the time to return to within some percentage of base pressure level, etc.

At step 530, the controller can determine whether the fluid pressure within the infusate flow pathway actually exhibited the aforementioned expected short-lived rise in the fluid pressure (which indicates that the infusion set is coupled to the user). If the infusion set is not coupled to the user, little back-pressure will exist and therefore the fluid pressure within the infusate flow pathway will not rise to the expected level during a dispensation. When such a scenario occurs, the controller can ascertain that the infusion set is not coupled to the user. Other measured metrics such as the shape of the pressure profile or the time to return to base pressure level may also be used to infer whether the infusion set is not coupled to the user.

A repetitious loop can exist between steps 530 and 510. That is, infusate dispensations and pressure data analysis can be repeated to ascertain accurate, ongoing knowledge (by the infusion pump controller) of whether the infusion set is coupled to the user.

At step 540, in response to an identification by the controller that the infusion set is not coupled to the user, the controller can initiate a notification to the user. Such a notification can be an alarm or alert of various types such as described above in regard to occlusion detection.

Timing Occlusion Alarms

In some cases, methods, devices, and systems provided herein can use different alarm thresholds for an occlusion detector based on data received from an analyte sensor. In some cases, methods, devices, and systems provided herein can use different alarm thresholds for an occlusion detector based on whether a bolus of medication has recently been delivered. In some cases, methods, devices, and systems provided herein can have an alarm threshold be adjusted based on the age of an infusion set. As such, the alarm thresholds in FIGS. 8A-8C can be shifted to the left or right based on data from an analyte sensor, data about the age of an infusion set, and/or data on recent medication delivery data. For example, in some cases, a changing or out-of-range analyte level may indicate that an occlusion condition is impacting the therapy regime for the patent and thus render a quicker remediation of the occlusion condition prudent, and thus an alarm threshold can be reduced in order to cause an occlusion alarm to trigger more quickly. In some cases, an analyte level being within range may indicate that the lack of delivery of medication is less dangerous, and thus the alarm threshold can be increased. For example, in the case of an insulin pump using data from a glucose monitor, a high or rising blood glucose level can cause an alarm threshold to be reduced, while a low or decreasing blood glucose level can be used to increase the alarm threshold and/or suspend insulin delivery. Additionally, a recent meal announcement can be considered in adjusting thresholds for a PWD. Additionally, some infusion sets for insulin pumps may have a intended use of between 2 and 7 days, and methods, systems, and devices may be adapted to receive data regarding when the infusion set was last changed, thus an alarm threshold may be reduced based on the age of the infusion set and/or whether or not it is older than a designated use life. Additionally, particular infusion sites may become more prone to occlusions as time passes, thus methods, systems, and devices may be adapted to receive data regarding the particular infusion site and how long it has been used, thus an alarm threshold may be reduced based on how long the particular infusion site has been used (e.g., the number of days it has been used).

In some cases, methods, devices, and systems provided herein can test a detected occlusion condition to determine if it is a self-resolvable occlusion condition and/or if it is the type of occlusion condition that requires user intervention. Accordingly, the test can determine if an occlusion alarm should be raised more quickly (e.g., if it requires user intervention) or if the alarm should be delayed in order to allow the occlusion condition to possibly self-resolve. In some cases, methods, devices, and systems provided herein can use analyte data to determine if the test is safe and/or whether it is safe to delay the alarm. In some cases, the test can include the administration of additional medication and an observation of occlusion sensor data to determine if a resulting increase in pressure (or force or change in light) indicates that the occlusion condition is complete and/or whether the occlusion condition is likely to self-resolve. For example, referring to FIG. 8A, a detection of light at a point between 811 and 812 can trigger an administration of one or more unit increments of medication to determine if the resulting change in light detected tracks the shape of curve 810. If there is a complete occlusion, a resulting light detected should move along curve 810, but if there is some release of pressure due to a partial occlusion, then the light detected will not by an amount corresponding to curve 810, which may indicate that medication is still be delivered and that the occlusion may self-resolve. Similarly, changes in pressure (FIG. 8B) and force (FIG. 8C) for a full occlusion corresponding to a delivery of one unit of medication would track curves 830 and 850 respectively for a complete occlusion. In some cases, the increase in pressure can cause the occlusion to self-resolve, thus a delay in testing the light, pressure, and/or force can be delayed for a predetermined amount of time. In some cases, an occlusion alarm can be triggered if a change in light, pressure, and/or force before and after a test delivery of medication is above a threshold. In some cases, the test administration of medication can be a next scheduled dose or can be an additional, non-scheduled dose of medication.

FIG. 10 illustrates an exemplary flow chart 600 of a method of delivering medication/infusate (e.g., insulin) and determining whether to sound an occlusion alarm. In step 610, infusate is administered to the user based on a user's demand, based on an algorithm, or based on a preprogrammed schedule. For example, if the infusate is insulin, the insulin can be a bolus of insulin delivered by the user for a meal or a correction, or the insulin can be basal insulin delivered according to a preprogrammed schedule, or the insulin can be automated insulin delivery based on a control algorithm using data from a glucose sensor. In step 620, a pressure in the fluid pathway (or in a medication reservoir) is detected. This can be detected directly or by reference to another type of occlusion detector that correlates to pressure (e.g., a light detecting occlusion detector or a force detector). In step 630, a processor can determine if a detected pressure (or detected light or force) exceeds a first threshold value. In some cases, the first threshold value can be a detection limit value, such as those depicted in FIGS. 8A-8C. If the detected pressure (or detected light or force) is less than a first threshold value, the process returns to step 610 for a subsequent delivery of medication.

If the detected pressure (or detected light or force) is at or greater than the first threshold value, the processor detects whether the pressure is above a second alarm threshold value in step 640, which can be the alarm thresholds depicted in FIGS. 8A-8C. As discussed above, the alarm thresholds can vary based on analyte data and/or recent administrations of medication. For example, an alarm threshold can be increased immediately after a bolus of insulin and/or decreased if a user's blood glucose data is elevated or rising. In some cases, an alarm threshold immediately after a new infusion site insertion can be increased to accommodate for the initial back pressure that a new infusion site typically provides. If the pressure is above the second alarm threshold, methods, devices, and systems provided herein can sound an occlusion alarm in step 645. In some cases, a sounded occlusion alarm can be audible, visual, and/or haptic.

If the detected pressure (or detected light or force) is less than the second alarm threshold value but above the first threshold value, then step 650 can determine if an additional administration of infusate is safe. This additional administration can be off schedule infusate delivery or delivery that is not based on the algorithm reference above for step 610. In some cases, the additional administration of infusate can be a minimum medication unit increment based on the infusion pump. In some cases, the additional administration of infusate can be an amount of medication calculated to result in a pressure exceeding the second alarm threshold value if the infusion pump is fully occluded. In some cases, the additional administration can be a maximum amount calculated to be safe according to a predictive algorithm, which may be limited to a maximum amount. For example, in the case of insulin being delivered using the pumps depicted in FIGS. 1-6C, 9A, and 9B, an amount of an additional delivery of insulin may be between 0.05 units of insulin and 0.5 units of insulin. In step 650, an additional delivery of medication (which can be a predetermined amount) can be determined to be safe if a predictive algorithm predicts that the delivery of the additional medication (plus all of a calculated MST as discussed above) would result in a dangerous condition. For example, if the infusate/medication is insulin, a predictive algorithm that adds IST and the additional administration (e.g., between 0.05 and 0.5 units) of insulin to an estimated IOB and determines if that administration will cause the PWD to experience a hypoglycemic condition using a predictive algorithm, which may assume the continuation of insulin delivered according to a preprogrammed schedule or according to an algorithm.

If the additional administration in step 660 is not safe, then the procedure 600 can return to step 610 for the next administration of medication according a user request, to an algorithm, or according to a schedule.

If the additional administration is safe in step 660, additional infusate is delivered in step 670. In step 680, a pressure (or force or light) is detected again, and step 690 determines if the pressure rise (or lack thereof) is consistent with an occlusion. In some cases, step 680 can occur immediately after step 670. In some cases, step 680 can be delayed for a predetermined period of time after step 670. In some cases, the delay can be between 1 second and 5 minutes. In some cases, the delay can be at least 5 seconds, at least 10 seconds, at least 30 seconds, or at least 1 minute. In some cases, the delay can be less than 5 minutes, less than 3 minutes, or less than 2 minutes.

Step 690 can determine if the pressure increase is consistent with a non-self-resolving occlusion. In some cases, the additional delivery of infusate is calculated to be an amount likely to send the pressure above the second alarm threshold value and step 690 can merely detect whether the pressure (or force or light) detected in step 680 is at or above the second alarm threshold value. In some cases, step 690 can analyze a change in pressure (or light or force) to see if it is consistent with a curve indicating a total occlusion, such as example curves 810, 830, and 850 depicted in FIGS. 8A-8C. In some cases, a threshold for determining whether to alarm in step 645 after step 690 is a pressure (or force or light) change that is a percentage of a change predicted by an occlusion curve, such as curves 810, 830, and 850. If the pressure rise is not sufficient to indicate an occlusion condition in step 690, then the procedure 600 can return to step 610 for the next administration of medication according a user request, to an algorithm, or according to a schedule. In some cases, step 690 can analyze the pressure change to see if it is approximately steady state to determine if the back pressure could be due to hydrostatic pressure, which may trigger a non-disruptive tip, notice, or query to the user regarding the relative heights of the infusion pump and the infusion site.

Exemplary Medication Delivery System

Methods, devices, and systems provided herein can be used to deliver any suitable medication, and can include an infusion pump of any appropriate design that includes some sensor designed to detect an occlusion condition. In some cases, the occlusion sensor is a pressure sensor, a force sensor, or a sensor that is adapted to detect other changes to correlate to a pressure increase in a medication reservoir and/or an infusion catheter. In the examples discussed below, the methods, devices and systems are used to deliver insulin.

Referring back to FIG. 1, an infusate delivery system can be diabetes management system (DMS) 10 that includes an infusion pump assembly 15, a mobile computing device 60, a continuous glucose monitor 50, and a blood glucose monitor 70. Infusion pump assembly 15 includes an infusion set 147 adapted to deliver an infusate (e.g., insulin) to an infusion site 146. As discussed above, the materials, lengths, and thicknesses (among other factors) of the infusion set 147 can impact the shapes of curves correlating pressure to a volume of medication stuck-in-transit (MST) (such as insulin stuck-in-transit (IST)). As shown, a mobile computing device 60, in wireless communication with insulin pump assembly 15, can serve as the primary user interface. As shown, mobile computing device 60 displays user interface home screen 300, which can allow a user to see actionable data and send commands to pump assembly 15. In some cases, a mobile computing device 60 can be absent (or optional) and the infusion pump assembly 15 can include a primary user interface.

In some cases, an analyte sensor, such as continuous glucose monitor 50, can be used as part methods, systems, and devices provided herein to automate medication delivery, change occlusion alarm thresholds, and/or determine whether an additional delivery of medication is safe. As shown, insulin pump assembly 15 is in wireless communication with continuous glucose monitor 50 and data from continuous glucose monitor 50 can be transferred to the mobile computing device 60 via insulin pump assembly 15. In some cases, a blood glucose meter 70 can be in wireless communication with infusion pump assembly 15. Alternatively, other methods and paths of communication are contemplated, including wired communication. In some cases, a continuous glucose monitor 50 can be incorporated into a single unit with an infusion pump assembly.

In some embodiments, DMS 10 can be a closed-loop insulin delivery system that uses glucose data from continuous glucose monitor 50 and/or blood glucose monitor 70 in one or more feedback loops to change basal delivery rates, update parameters, settings, and/or models for dosage delivery that are specific to the user. In some cases, a pump controller (e.g., pump controller 200) is part of pump assembly 15 and includes one or more processors adapted to alter basal delivery rates, change parameters, settings and/or models for dosage delivery based on glucose data from a continuous glucose monitor 50 and/or a blood glucose meter 70. In some cases, algorithms for changing basal delivery rates, update parameters, settings, and/or models for dosage delivery that are specific to the user can be present on mobile computing device 60 and/or on a remote server that is accessed by the mobile computing device 60 via the cloud.

Occlusion alarms or alerts discussed herein can be sounded using any suitable manner, which can include one or more of audible tones, haptic feedback, and/or visual indications, which can come from the pump assembly 15, mobile computing device 60, CGM 50, and/or BGM 70. In some cases, pump assembly 15 can include between one or more LED indicators adapted to light to inform the user of certain conditions, which can include an occlusion condition. In some cases, mobile computing device 60 can provide troubleshooting tips and/or instructions regarding how to resolve an occlusion if an occlusion alarm sounds. In some cases, the troubleshooting tips can include an audiovisual presentation illustrating one or more of (a) a depiction of how to check for kinks in an occlusion catheter; (b) checking the infusion site; (c) instruction to change the infusion set; and/or (d) questions about the last time the occlusion set was changed. Alternatively, the infusion pump assembly can include robust user interface that can provide the user with text instructions or suggestions regarding how to fix an occlusion.

In some cases, methods, systems, and devices provided herein can track when an infusion set was last changed and change alarm thresholds based on length of time that the infusion set has been used. In some cases, an infusion set age can be estimated based on actions that the user takes to prime the cannula of the infusion set (e.g., fill the infusion set catheter with infusate). In some cases, methods, devices, and systems provided herein can ask the user to input infusion set changes. Changing alarm thresholds based on infusion set age can improve user compliance with the labeled use of an infusion set. Additionally, non-self-resolving occlusions can become more common as an infusion set ages. In some cases, a troubleshooting guide provided to the user during/after an occlusion alarm can be different based on the age of an infusion set.

Mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices. In some cases, mobile computing device 60 can be used to transfer data from controller device 200 to the cloud. In some cases, the mobile computing device 60 provides a user interface (e.g., graphical user interface (GUI), speech-based user interface, motion-controlled user interface) through which users can provide information to control operation of the controller device 200 and the insulin delivery system 10. For example, the mobile computing device 60 can be a mobile computing device running a mobile app that communicates with the controller device 200 over short-range wireless connections (e.g., BLUETOOTH connection, Wi-Fi Direct connection) to provide status information for the insulin delivery system 10 and to allow a user to control operation of the insulin delivery system 10 (e.g., toggle between delivery modes, adjust settings, log food intake, confirm/modify/cancel bolus dosages, and the like).

Continuous glucose monitor 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In some cases, the sensor shaft 56 can measure glucose or another analyte in interstitial fluid or in another fluid and correlate that to blood glucose levels. In response to the measurements made by the sensor shaft 56, continuous glucose monitor 50 can employ the wireless communication device 54 to transmit data to a corresponding wireless communication device 247 housed in the pump system 15. In some cases, the monitoring device 50 may include a circuit that permits sensor signals (e.g., data from the sensor shaft 56) to be communicated to the communication device 54. The communication device 54 can transfer the collected data to the controller device 200 (e.g., by wireless communication to the communication device 247). Alternatively, the monitoring device 50 can employ other methods of obtaining information indicative of a user's blood characteristics and transferring that information to the controller device 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. Invasive methods involving optical means of measuring glucose could also be added. In yet another example, the monitoring device can include an optical detection instrument that is inserted through the skin for measuring the user's glucose level. Furthermore, it should be understood that in some alternative implementations, the monitoring device 50 can be in communication with the controller device 200 or another computing device via a wired connection.

DMS 10 may optionally communicate with blood glucose meter 70 in addition to (or as an alternative to) continuous glucose meter 50. For example, one or more test strips (e.g., blood test strips) can be inserted into a strip reader portion of blood glucose meter 70 and then receive blood to be tested. In some cases, blood glucose meter 70 is configured to analyze the characteristics of the user's blood and to communicate (e.g., via a Bluetooth wireless communication connection) the information to the controller device 200. In some cases, a user can manually input a glucose meter reading. Blood glucose meter 70 can be manually operated by a user and may include an output subsystem (e.g., display, speaker) that can provide the user with blood glucose readings that can be subsequently entered into the controller or user interface (to collect the data from an unconnected BGM into the system). Blood glucose meter 70 may be configured to communicate data (e.g., blood glucose readings) obtained to the controller device 200 and/or other devices, such as the mobile computing device 60. Such communication can be over a wired and/or wireless connection, and the data can be used by the controller device 200 and/or the mobile computing device 60 to perform multiple delivery modes and/or a secondary feedback loop for the insulin delivery system 10.

DMS 10 may include one or more external medication delivery devices 80 (e.g., syringe, an insulin pen, a smart syringe with device communication capabilities, or the like) through which additional medicine dosages (e.g., insulin, glucagon) can be manually administered to a user. In some cases, user interfaces provided herein allow users to input a medication, a dosage amount, and the timing so that a closed-loop control algorithm can account for the additional medication. In some cases, mobile computing device 60 can make a recommendation for an amount of insulin to be delivered using an external delivery device.

Still referring to FIGS. 1, 2A, and 2B, in some embodiments pump assembly 15 can include pump device 100 configured to removably attach to the controller device 200 in a manner that provides a secure fitting, an overall compact size, and a reliable electrical connection. Pump assembly 15 can be pocket-sized so that the pump device 100 and controller device 200 can be worn in the user's pocket or in another portion of the user's clothing. In some circumstances, the user may desire to wear the pump assembly 15 in a more discrete manner. Accordingly, the user can pass the tube 147 from the pocket, under the user's clothing, and to the infusion site where the adhesive patch can be positioned. As such, the pump assembly 15 can be used to deliver medicine to the tissues or vasculature of the user in a portable, concealable, and discrete manner.

In some cases, the pump assembly 15 can be configured to adhere to the user's skin directly at the location in which the skin is penetrated for medicine infusion. For example, a rear surface of the pump device 100 can include a skin adhesive patch so that the pump device 100 can be physically adhered to the skin of the user at a particular location. In these cases, the cap device 130 can have a configuration in which medicine passes directly from the cap device 130 into an infusion set 146 that is penetrated into the user's skin. In some examples, the user can temporarily detach the controller device 200 (while the pump device 100 remains adhered to the skin) so as to view and interact with the user interface 220.

The pump device 100 in this example includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (e.g., including a battery powered actuator, a gear system, a drive rod, and other items that are not shown) that advances a plunger 125 in the fluid cartridge 120 so as to dispense fluid therefrom. In this example, the controller device 200 communicates with the pump device 100 to control the operation of the drive system. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device (having a new fluid cartridge) to the reusable controller device 200 for the dispensation of fluid from a new fluid cartridge. Accordingly, the user is permitted to reuse the controller device 200 (which may include complex or valuable electronics, as well as a rechargeable battery) while disposing of the relatively low-cost pump device 100 after each use. Such a pump assembly 15 can provide enhanced user safety as a new pump device (and drive system therein) is employed with each new fluid cartridge. Additional and/or alternative implementations of the controller device 200 are also possible, including magnetic drive turbine (MDT) monolithic architecture pumps and/or omnipods.

The pump assembly 15 can be a medical infusion pump assembly that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a fluid cartridge 120 in the form of a carpule that is preloaded with insulin or another medicine for use in the treatment of Diabetes (e.g., Exenatide (BYETTA, BYDUREON) and liraglutide (VICTOZA)SYMLIN, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some cases, the pump device 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of the pump device 100. In some cases, the retainer wings can interfere with attempts to remove the fluid cartridge 120 from the pump device 100, thus ensuring that the pump device 100 will be discarded along with the fluid cartridge 120 after the fluid cartridge 120 is emptied, expired, or otherwise exhausted. In another example, the cap device 130 can be configured to irreversibly attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the fluid cartridge 120 is emptied, expired, or otherwise exhausted).

Referring to FIGS. 2A and 2B, the controller device 200 can be removably attached to the pump device 100 so that the two components are mechanically mounted to one another in a fixed relationship. In some cases, such a mechanical mounting can also form an electrical connection between the removable controller device 200 and the pump device 100 (for example, at electrical connector 118 of the pump device 100). For example, the controller device 200 can be in electrical communication with a portion of the drive system (show shown) of the pump device 100. In some cases, the pump device 100 can include a drive system that causes controlled dispensation of the medicine or other fluid from the cartridge 120. In some cases, the drive system incrementally advances a piston rod (not shown) longitudinally into the cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device 130 to the housing structure 110. Thus, when the pump device 100 and the controller device 200 are mechanically attached and thereby electrically connected, the controller device 200 communicates electronic control signals via a hardwire-connection (e.g., electrical contacts along connector 118 or the like) to the drive system or other components of the pump device 100. In response to the electrical control signals from the controller device 200, the drive system of the pump device 100 causes medicine to incrementally dispense from the fluid cartridge 120. Power signals, such as signals from a battery (not shown) of the controller device 200 and from the power source (not shown) of the pump device 100, may also be passed between the controller device 200 and the pump device 100.

Cap device 130 of the pump device 100 can be configured to mate with an infusion set 146. In general, the infusion set 146 can be a tubing system that connects the pump assembly 15 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 2) of the fluid cartridge 120 and the tube 147 of the infusion set 146.

First Exemplary Occlusion Detector

Referring now to FIGS. 3A-6C, the pump assembly 15 can be equipped with a pressure sensor as part of cap 130 that detects pressures in the infusate fluid flow path extending to the user. For example, the controller device 200 may include an optical sensor system 250 that detects the amount of light reflected from a portion of the cap device 130. In this embodiment, the optical sensor system 250 can detect changes in the amount of light reflected from the cap device 130 in response to an occlusion that causes an increase in the fluid pressure in the infusate fluid flow path. For example, as described below in connection with FIGS. 6A-6C below, the optical sensor system 250 may operate using the principle of total internal reflection.

Figure 3A:
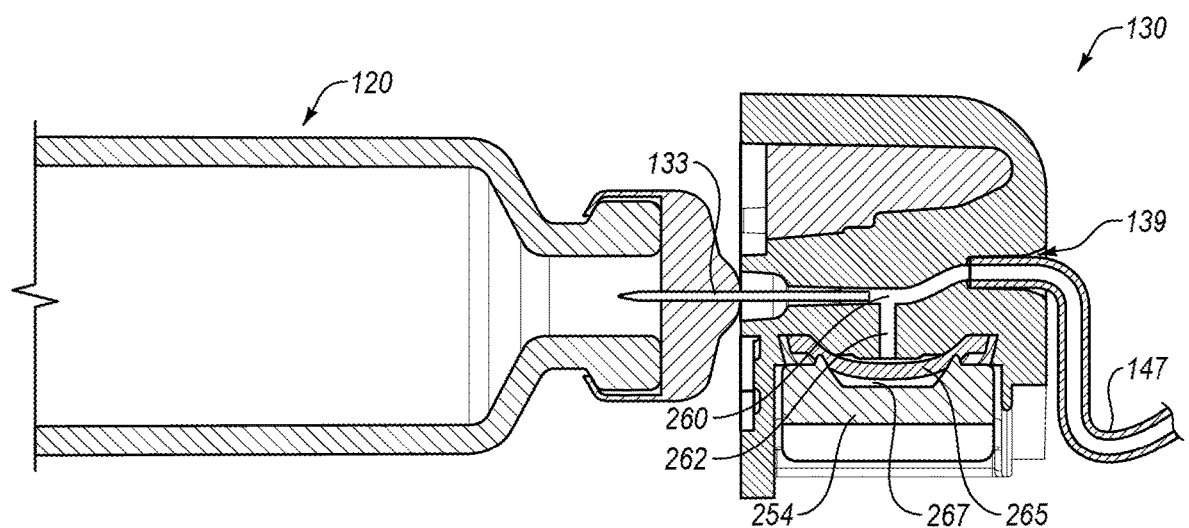
FIGS. 3A and 3B are schematic diagrams of an exemplary occlusion sensor.

Referring to FIG. 3A, the cap device 130 can have a multi-piece construction that provides a flow path from the medicine container 120 to the infusion set tubing 147 (e.g., via an output port 139). At least a portion of the flow path through the cap device 130 may be monitored by the occlusion detection system 250 to determine if an occlusion exists downstream of the cap device 130 using the methods and procedures described herein. The multi-piece construction of the cap device 130 can facilitate proper alignment of the cap device 130 and proper engagement with the medicine cartridge 120 during attachment of the cap device 130 to the pump housing 110. For example, during attachment of the cap device 130 to the pump housing, a needle penetrator 133 attached to a portion of the cap device can be advanced toward the septum of the medicine cartridge 120 to pierce the septum and open a fluid flow path. The flow path for the medicine that is dispensed from the medicine cartridge 120 can pass through the needle penetrator 133, through a fluid channel 260 (described below), through the infusion set tubing 147, and to the user.

The fluid channel 260 arranged in the cap device 130 may include a secondary channel 262 that extends to a flexible member 265. In this embodiment, one side of the flexible membrane 265 is exposed to the fluid channel 260 (via the secondary channel 262) while the opposite side of the flexible membrane 265 is adjacent to an air cavity 267, which provides a volume into which the flexible membrane 265 can expand as pressure rises in the fluid channel 260. The flexible membrane 265 may comprise a flexible polymer material that bulges or otherwise deforms as the fluid pressure in the flow channel 260 rises and is preferably composed of silicon. As such, the flexible membrane 265 can flex into the air cavity 267 when the fluid pressure rises due to an occlusion in the flow path downstream of the fluid channel 260.

Figure 3B:
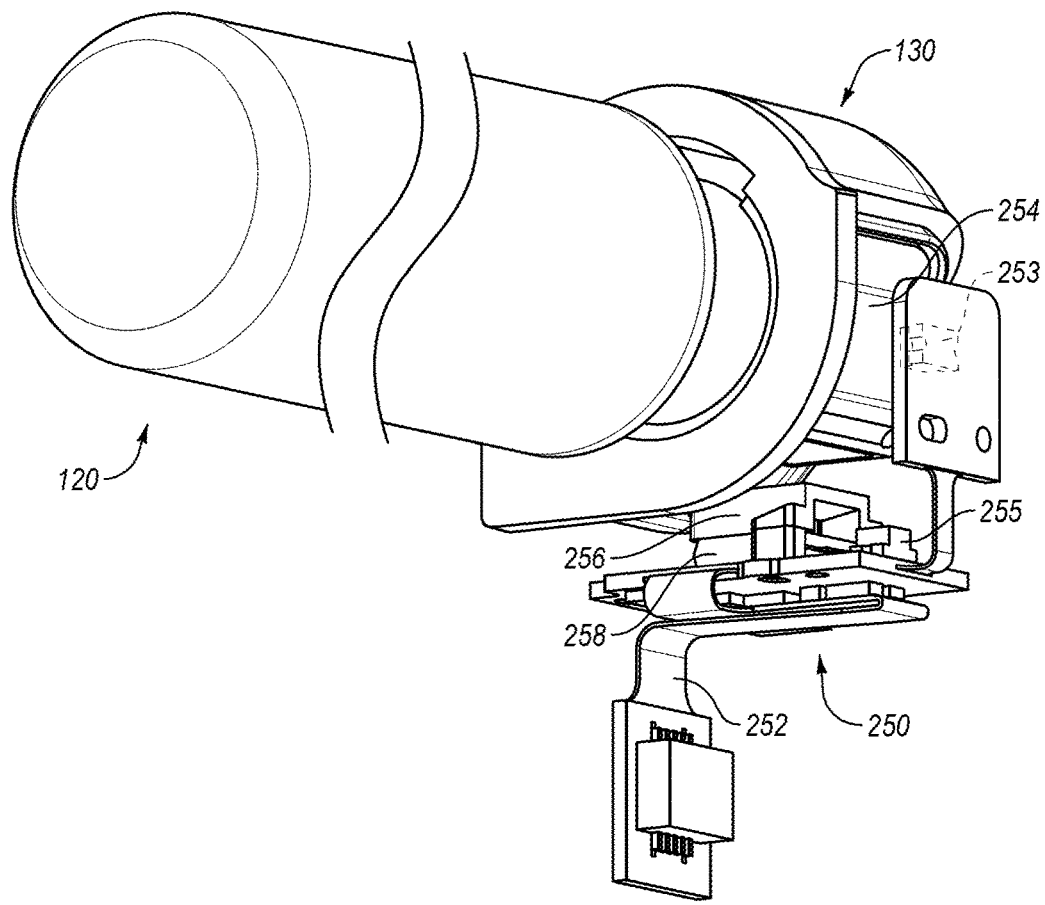

Referring to FIG. 3B, the occlusion detection system 250 may include a number of components that are housed in the controller device 200. For example, the occlusion detection system 250 may include one or more light emitters and a light sensor arranged on the sensor circuit 252 that is housed by the controller device 200, thereby permitting these components to be reused along with the controller device (while the relatively low cost components in the pump device 100 are discarded after the "one time use" of the pump device 100). In a preferred embodiment, the sensor circuit 252 includes a primary light emitter 253, a reference light emitter 255, and a light sensor 258.

The sensor circuit 252 can be arranged so that the cap device 130 is aligned with the light emitters 253, 255 and the light sensor 258 when the pump device 100 is attached to the controller device 200. It should be understood that the pump housing 110 and the controller housing 210 have been removed from FIG. 9 for purposes of showing the relative position of the sensor circuit 252 (in the controller device 200 as shown in FIGS. 2 and 4) and the cap device 130 (attached to the pump housing 110 as shown in FIG. 1).

The sensor circuit 252 can be connected to the control circuitry 240 of the controller device 200 (FIG. 6) via a flexible circuit substrate or one or more wires. In a preferred embodiment, the sensor circuit 252 connects with the main processor board 242 via the flexible circuit substrate illustrated in FIG. 6. As such, the control circuitry 240 can receive sensor signals and employ detection software stored in one or more memory devices 242 to determine if an occlusion exists. If the sensor signals from the occlusion detection system 250 indicate that an occlusion exists in the fluid flow path, the controller device 200 can trigger an alert to inform the user. The alert may include a visual or audible alarm communicated via the user interface 220 of the controller device 200.

The light collector 256 can be made of any reflective material, preferably polished aluminum, and is designed to collect light from both the reference light emitter 255 and the primary light emitter 253. For example, apertures are advantageously constructed in the light collector 256 to allow light to reach the light sensor 258 from specific directions corresponding to light originating from the reference light emitter 255 and from the primary light emitter 253.

In some embodiments, the reference light emitter 255 can provide a reference light reading at the sensor 258, which can be advantageously compared to a light reading from the primary light emitter 253 for purposes of determining when a reduced light reading from the main emitter 253 is caused by a buildup of fluid pressure in the fluid channel 260 (e.g., from an occlusion in the infusion set tubing 147) or is caused by some other reason not related to the presence of an occlusion (e.g., environmental conditions such as ambient temperature). For example, in some embodiments, the amount of light emitted from the primary emitter 253 begins to degrade or otherwise changes with fluctuations in ambient temperature and ambient light condition. If the control circuitry was configured to rely upon the light sensor readings detected by the light sensor 258 from the primary emitter 253 alone, such reductions in the amount of the light readings from the primary light emitter 253 would possibly induce false occlusion warnings (e.g., occlusion alerts where in fact the suboptimal temperatures are responsible for the reduced light readings and no occlusion is present in the infusion set tubing 147). In this embodiment, each of the primary emitter 253 and the reference light emitter 255 are substantially equally affected by the fluctuations in ambient temperature and ambient light condition. Accordingly, a comparison of the amount of the light received from the primary light emitter 253 with the amount of the light received from the reference light emitter 255 (rather than an absolute light measurement from the primary light emitter 253 alone) can be employed to substantially reduce or eliminate the number of false occlusion warnings.

Figure 4A:
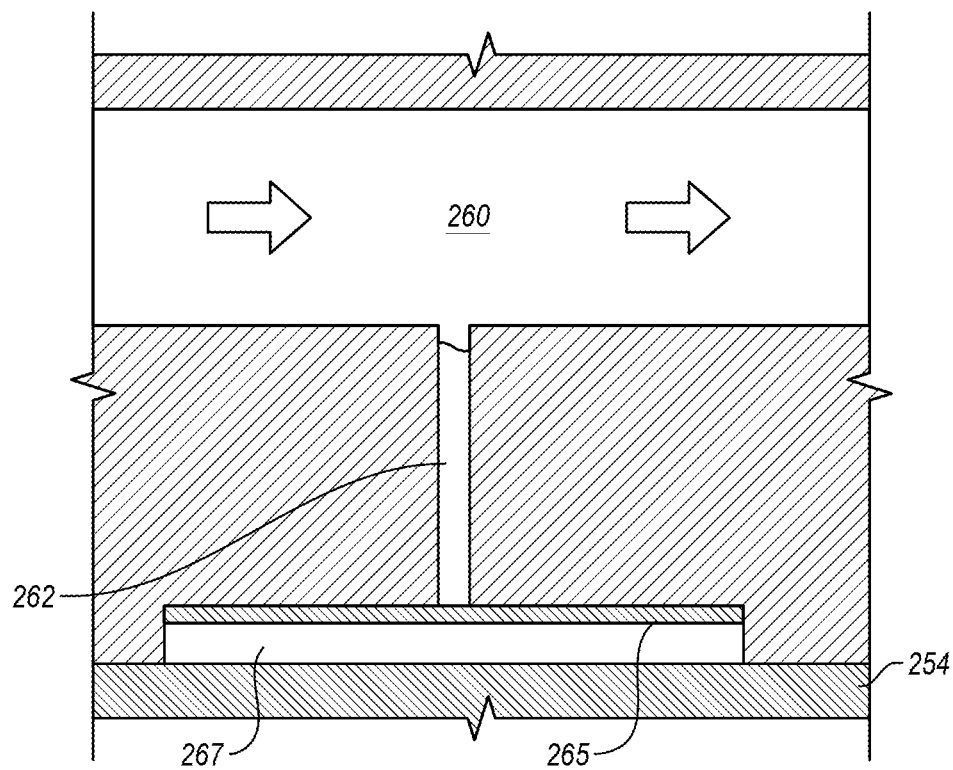
FIGS. 4A and 4B are cross-sectional views of a portion of a fluid channel for the sensor of FIGS. 3A and 3B.
Figure 4B:
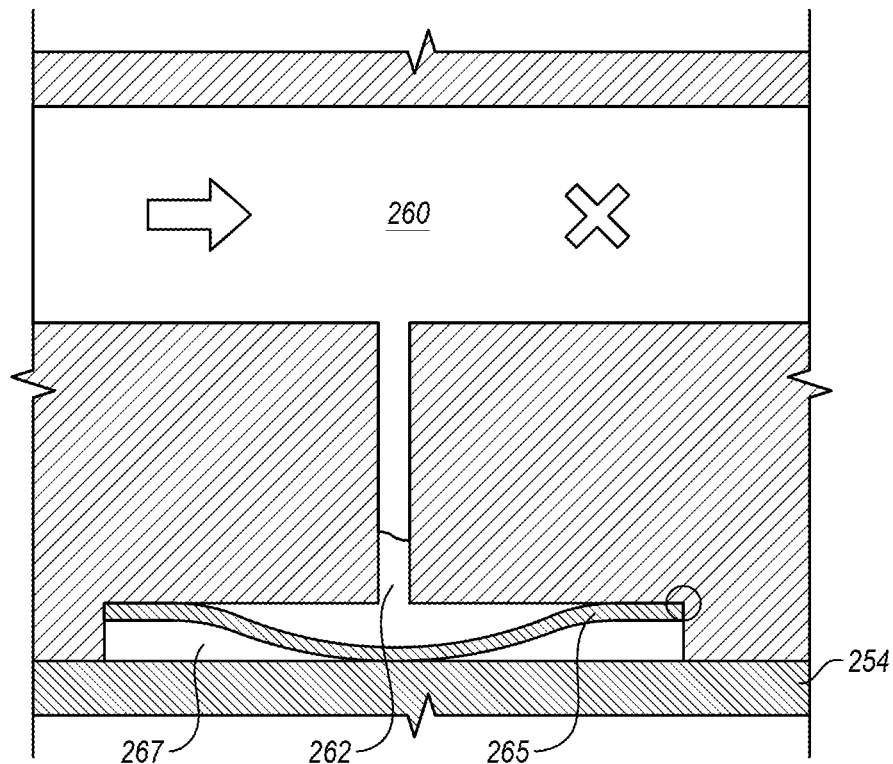

FIGS. 4A and 4B depict what happens when there is an occlusion in the device of FIGS. 3A and 3B. FIG. 4A depicts the normal operation of flow channel 260 when there is not an occlusion, represented by the two arrows. As shown, flexible membrane 265 is not expanded into air cavity 267, thus light is internally reflected when it meets the interface between internal light transmissive member 254 and air cavity 267. If there is an occlusion, as shown in FIG. 4B (illustrated by the X), fluid presses into secondary channel 262 to cause flexible membrane 265 to expand and press against the internal light transmissive member 254, which can cause the light to not reflect. The thickness of air cavity 267 can determine the sensitivity of the sensor. For example, referring back to FIG. 8A, the length of curve segment 815 can be changed, thus the detection limit can be changed, by changing the thickness of air cavity 267. Additionally, the flexibility and elasticity of flexible membrane 265 can change the sensitivity of the sensor. After the pressure increases such that any portion of the flexible membrane 265 touches internal light transmissive member 254, additional pressure will cause the diameter of the portion of flexible membrane 265 touching internal light transmissive member 254 to expand, thus less light will be reflected with increasing pressures. FIG. 8A depicts a possible correlation between an amount of light reflected (listed as a percentage) and an approximate pressure within flowpath 260.

Figure 5:
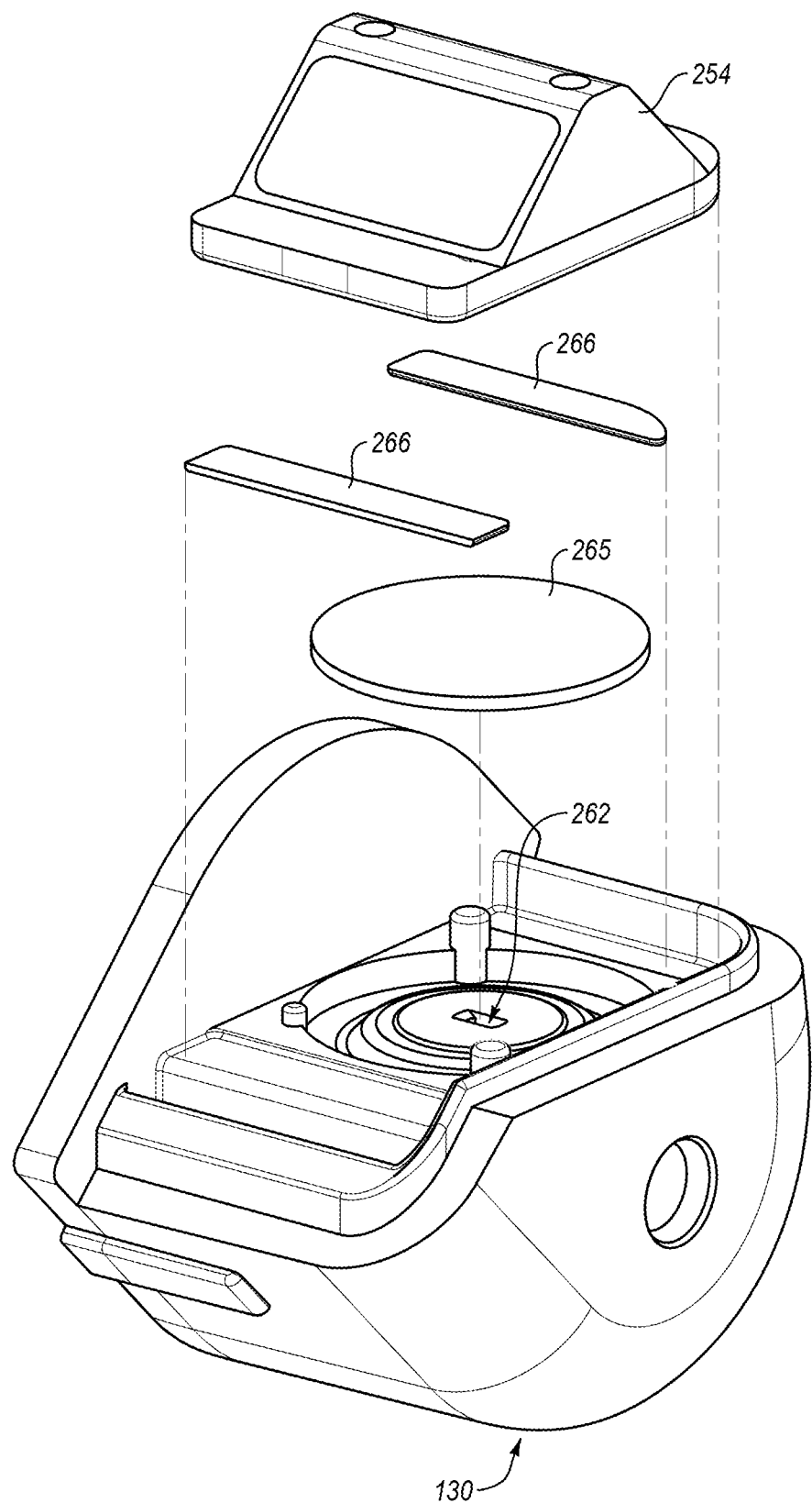
FIG. 5 depicts the details of a cap device of FIGS. 2A and 2B including an occlusion sensor.

FIG. 5 is an exploded view of the cap device 130, in accordance with some embodiments. Internal transmissive member 254 can be affixed to the remaining components of the cap device 130 using a bonding material 266, such as an adhesive film or glue. The flexible membrane 265 is positioned to form a seal between the fluid channel 262 and light transmissive member 254. That is, once the flexible membrane 265 is assembled into the cap device 130, the flexible membrane 265 deforms in response to a buildup of fluid pressure in the fluid path 260 (which is communicated via the secondary channel 262), but does not allow fluid in the fluid channel 260 to escape pass the membrane 265 into the air cavity 267 or otherwise interfere with other components of the pump device 100 or the controller device 200.

Figure 6A:
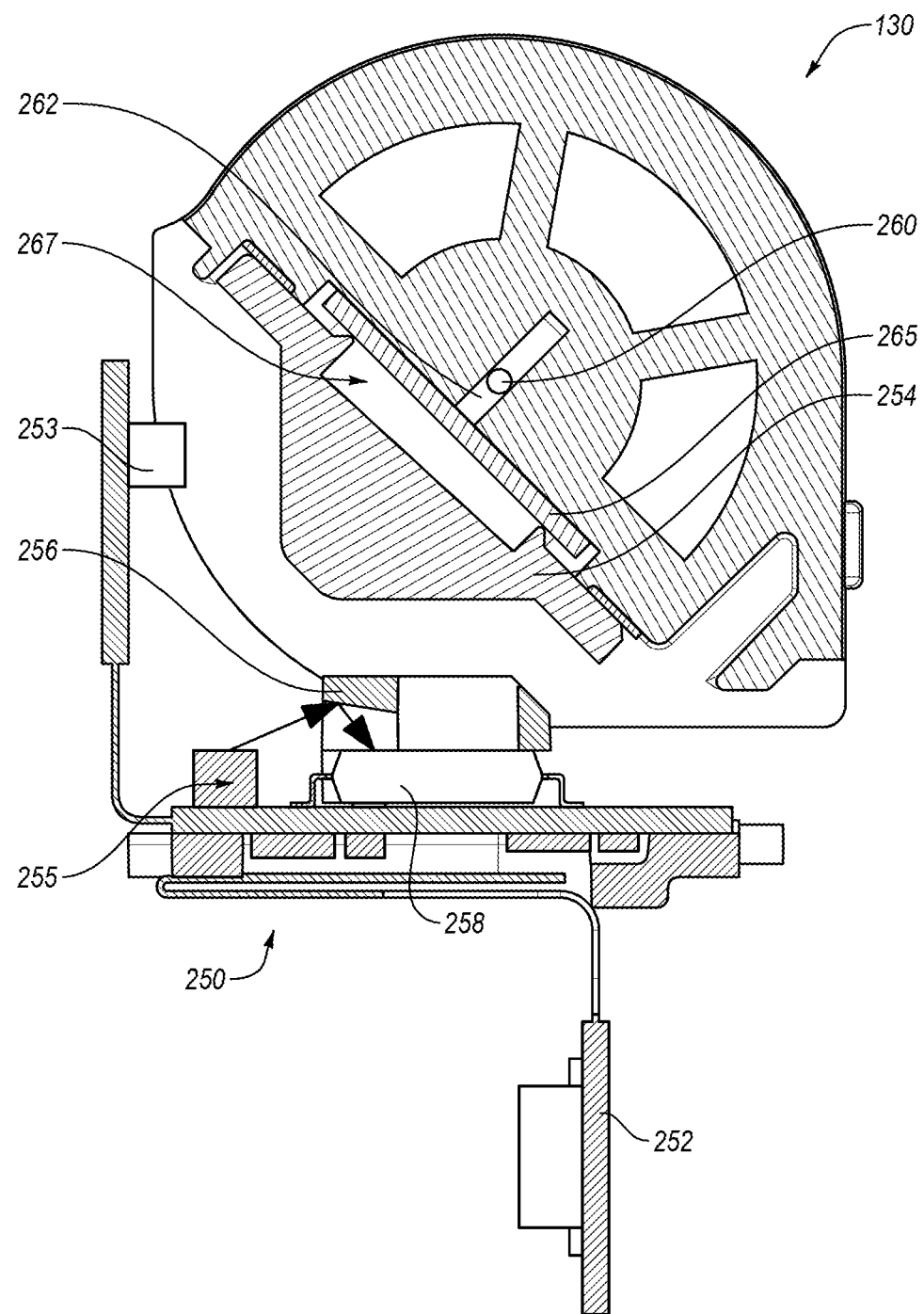
FIGS. 6A-6C illustrate examples of how light can be directed at the occlusion sensor of the cap device of FIG. 5 to detect occlusions.
Figure 6B:
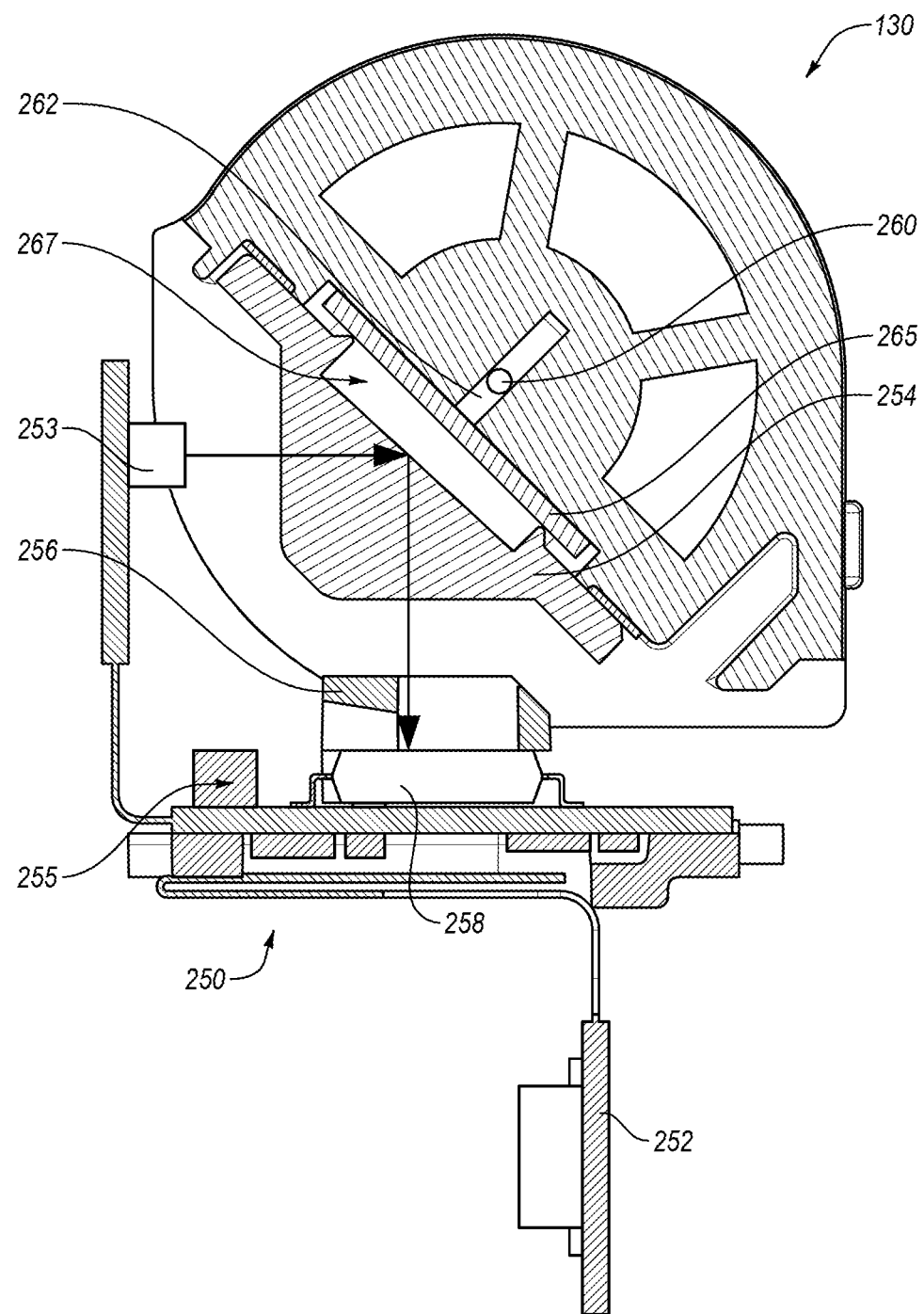
Figure 6C:
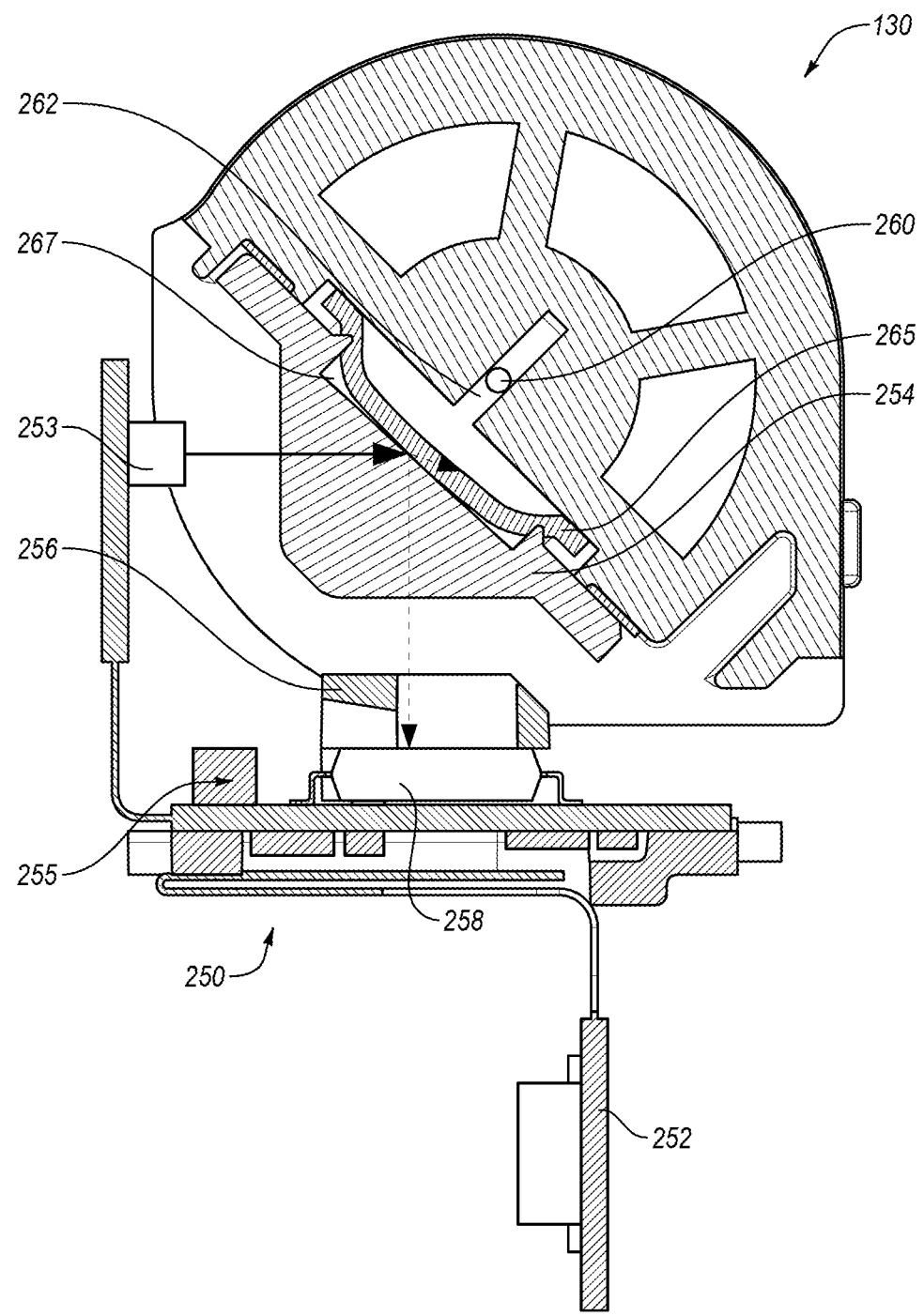
Figure 7:
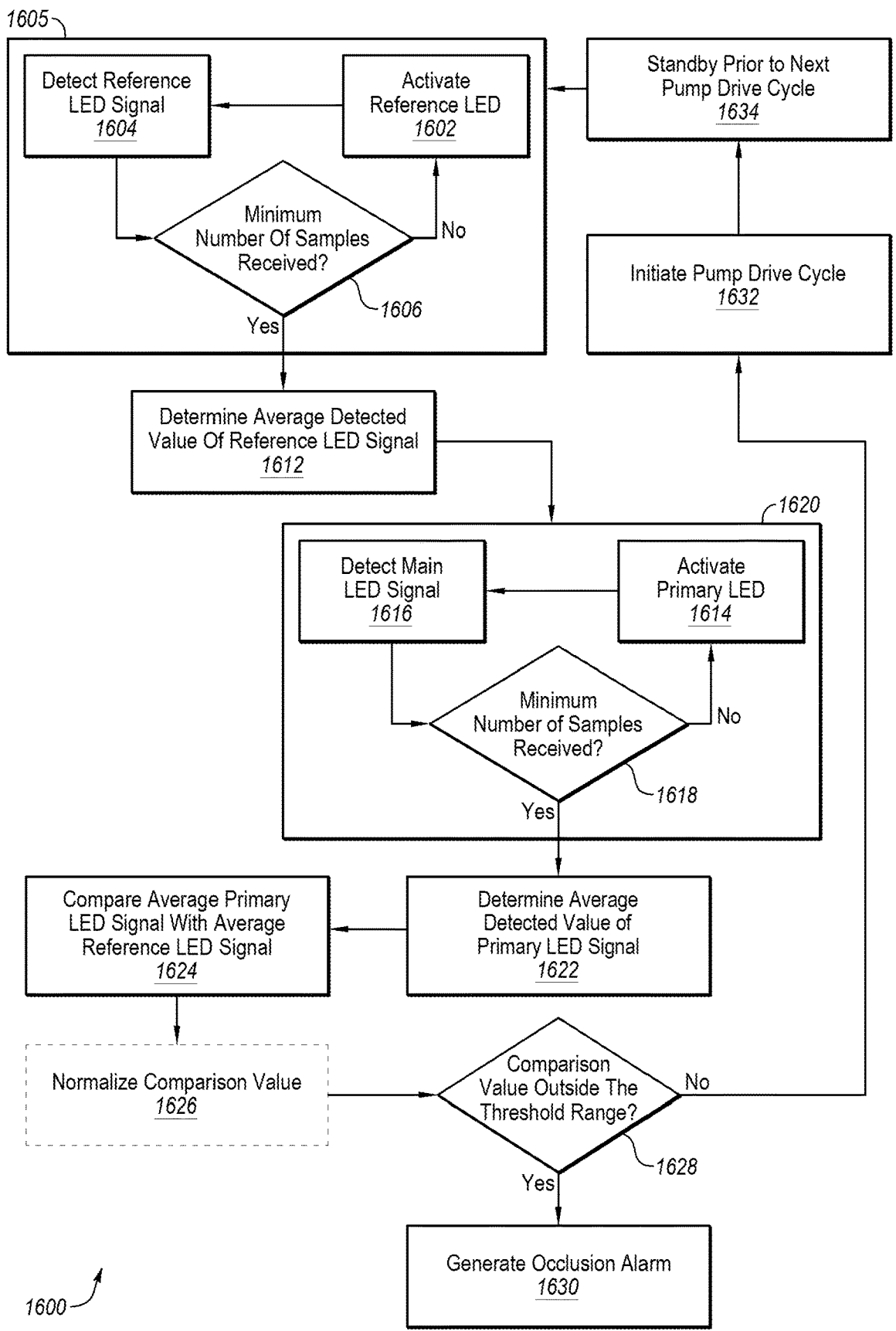
FIG. 7 is a flowchart of an example method for using the occlusion sensor to generate an occlusion alarm.

FIGS. 6A-6C illustrate how the light works in the occlusion detector. FIG. 7 is a flow chart illustrating a method of detecting an occlusion. As shown in FIGS. 6A and 6B, when no substantial pressure exists in the flow path, the medicine can be dispensed under normal operating conditions from the medicine cartridge 120, through the cap device 130, and into the infusion tubing 147. As such, the flexible membrane 265 that is adjacent to the fluid channel 260 is not substantially deformed such that it deforms to touch internal light transmissive member 254, thus the occlusion detector 250 does not detect any pressure. Referring to FIG. 6A, in some embodiments, the occlusion sensor 250 may operate by activating the reference light emitter 255 in isolation from the primary light emitter 253. When the reference light emitter 255 is activated, the light is received by the light collector 256 and directed toward the light sensor 258 without passing through the light transmissive member 254 or any other portion of the cap device 130. For example, as shown in FIG. 6A, at least a portion of the light from the reference emitter 255 (e.g., a wide-angle LED emitter in this embodiment) reflects off a surface of the light collector 256 and is received by the light sensor 258. In some cases, a generally opaque portion of the controller housing 210 may optionally prevent the light from the reference emitter 255 from passing outside the controller housing 210. Here, because the reference light emitter 255 does not transmit light through the light transmissive member 254, the amount of light transmitted by the reference light emitter 255 and received by the light sensor 258 is generally unaffected by a buildup of fluid pressure in the fluid channel 260 (as will be described in more detail in reference to FIGS. 6B and 6C).

In other words, the amount of light emitted by the reference emitter 255 and received by the light sensor 258 does not fluctuate according to fluid pressure but may fluctuate according to other environmental factors, such as ambient temperature (and it should be understood that primary light emitter 253 is similarly affected by these same environmental factors). This configuration can be employed to aid in the detection of an occlusion that accounts for changes in environmental factors affecting the primary light emitter 253. For example, when the infusion pump assembly 15 is operating in regions having lower ambient temperatures, both the reference light emitter 255 and the primary light emitter 253 will have reduced light outputs. In those circumstances, the occlusion detection system 250 can use the reduction in the amount of light from the reference light emitter 255 to account for the reduction in the amount of light from the primary light emitter 253. In other circumstances in which the light sensor 258 receives a reduced light signal only from the primary light emitter 253 while the light sensor 258 receive a normal light signal from the reference light emitter 255, then there is a greater likelihood of the presence of an occlusion and the user may be warned accordingly.

Referring to FIG. 6C, when the medicine flow path is in a non-occluded state under normal operating circumstances, the light from the light emitter 253 can be reflected at the interface where the internal light transmissive member 254 meets the air cavity 267. In some embodiments, this light reflection may occur due to total internal reflection that the interface. Total internal reflection can occur in some circumstances when light passes through a first medium (e.g., the internal light transmissive member 254) and strikes an interface between the first medium and a second medium (e.g., the air cavity 267) at an angle greater than the critical angle. If the refractive index of the second medium (e.g., the air cavity 267) is lower than refractive index of the first medium (e.g., the internal light transmissive member 254), the light may undergo total internal reflection within the first medium.

For example, as shown in FIG. 6B, the light emitter 253 can be an infrared light emitter that is directed toward the internal light transmissive member 254. The infrared light passes through the generally transparent first window 136 and then transmits through the light transmissive member 254. In some embodiments, the surface of the light transmissive member 254 may be curved and may operate as a focusing lens that directs the infrared light toward the air cavity 267 proximate to the fluid channel 260, although a non-curved surface is shown for the embodiments of FIGS. 6A-6C.

Referring still to FIG. 6B, when the medicine is dispensed under normal operating conditions below a detection limit (see FIG. 8A), the flexible membrane 265 does not flex downwardly into the air cavity 267 to abut the internal light transmissive member 254. Accordingly, the infrared light passing through the internal light transmissive member 254 reflects at the interface where the internal light transmissive member 254 meets the air cavity 267. This reflected light continues through the internal light transmissive member 254 toward the light sensor 258. In this embodiment, the reflected light transmitted through the light transmissive member 254 passes through the second window 138 (shown in FIG. 10) and is subsequently received by the light collector 256 (described in reference to FIG. 9) and directed toward the light sensor 258. The light sensor 258 may comprise an infrared photo detector that is capable of converting the receipt of infrared light into electrical signals. These electrical signals from the light sensor 258 can be transmitted via the sensor circuit 252 to the control circuitry 240 (FIG. 6) for processing to determine if an occlusion alarm should be provided to the user.

Referring to FIG. 6C, when pressure in the flowpath exists exceeds a detection limit, the flexible membrane 265 can expand into air cavity 267 and touch internal light transmissive member 254, which can result in less light reflecting. As pressure builds, the area of the flexible membrane 265 touching internal light transmissive member 254 increases, thus less light is reflected. FIG. 6C illustrates the reduction of measurable light with dotted lines. FIG. 8A, discussed above, shows a hypothetical curve 810 for this arrangement, where a percentage of light reflected along the right axis corresponds to a pressure (left axis) and a number of clicks of insulin (bottom axis). For example, if pump device 100 attempts to dispense another incremental dosage of medicine when the infusion set tubing 147 is clogged or kinked, the fluid pressure upstream of the occlusion (e.g., in the medicine cartridge 120 and in the cap device 130) may be increased. As discussed above, occlusion alarm thresholds can be greater than the detection threshold, and can be variable, so that users do not become annoyed with unnecessary alarms.

FIG. 7 show process 1600 that can be performed for purposes of detecting the presence of an occlusion or elevated pressure in the medicine flow path to the pump user. The process 1600 may be at least partially implemented in an occlusion detection software algorithm that is stored on a memory device and executed by a processor of the control circuitry. In this embodiment, the control circuitry 240 may implement a first iterative step shown by box 1605 so to activate the wide-angle reference light emitter 255 to turn on in step 1602. For example, because the control circuitry 240 is in electrical communication with the reference light emitter 255, the control circuitry 240 can generate an electrical signal that when received by the wide-angle reference light emitter 255 causes the wide-angle light emitter 255 to emit light. In addition, the absence of the electrical signal may cause the reference light emitter 255 to deactivate.

In a step shown by box 1604, the control circuitry 240 detects a signal corresponding to the light emitted by the reference light emitter 255 and received by the light sensor 258. For example, light transmitted from the reference light emitter 255 may reflect off of the interior surface of the light collector 256 and interact with the light sensor 258. As described in more detail above, the light sensor 258 can generate an electrical signal corresponding to the received light. Because the control circuitry 240 is in electrical communication with the light sensor 258, the control circuitry 240 detects the signal corresponding to the light emitted by the wide-angle reference light emitter 255 when the control circuitry 240 receives the electrical signal from the light sensor 258. In a preferred embodiment, each of the detected signals corresponding to light emitted by the reference light emitter 255 is a floating point value within the range of [0-1] and is stored on one more dedicated memory devices included in the control circuitry 240.

In a decision shown by step 1606, the control circuitry 240 determines whether a minimum number of light samples transmitted by the wide-angle light emitter 255 has been received. For example, in a preferred embodiment, the control circuitry 240 determines whether sixteen iterations of activating the reference emitter 255 and detecting the corresponding sixteen electrical signals from the light sensor 258 have been completed. If the minimum number of light samples has not been received, than the control circuitry 240 may instruct the reference light emitter 255 to activate again, repeating the steps included in the first iterative step shown by box 1605. In this embodiment, the sixteen iterations can be consecutive performed in a period of 0.5 seconds or less.

Once the minimum number of light samples has been received (e.g., sixteen in this embodiment), the control circuitry 240 may perform operation 1612 to determine an average detected value of the reference light emitter samples received. For example, in a preferred embodiment, because the control circuitry 240 receives sixteen light samples from the reference light emitter 255, the sixteen light samples are added together and the total divided by sixteen to determine the average detected value of the wide-angle reference samples received. In a preferred embodiment, the determined average value corresponding to light transmitted by the reference light emitter 255 is a floating point value within the range of [0-1] and is stored on one or more dedicated memory devices included in the control circuitry 240.

In a second iterative step shown by box 1620, the control circuitry 240 activates the primary light emitter 253 as shown in a step 1614. For example, because the control circuitry 240 is in electrical communication with the primary light emitter 253, the control circuitry 240 can generate an electrical signal that when received by the primary light emitter 253 activates the primary light emitter 253 to emit light. In addition, the absence of the electrical signal may instruct the primary light emitter 253 to deactivate.

In a step 1616, the control circuitry 240 can detect a signal corresponding to the light emitted by the primary light emitter 253 and received at the light sensor 258. For example, the light transmitted from the primary light emitter 253 that passes through the light transmissive member 254, may be reflected by the interface between the light transmissive member 254 and the air cavity 267 toward the light sensor 258. As described in more detail above, the light sensor 258 can generate an electrical signal corresponding to the received light. Because the control circuitry 240 is in electrical communication with the light sensor 258, the control circuitry 240 detects the signal corresponding to the light emitted by the primary light emitter 253 when the control circuitry 240 receives the electrical signal from the light sensor 258. In a preferred embodiment, each of the detected signals corresponding to the light emitted by the primary light emitter 253 is a floating point value within the range of [0-1] and is stored on one more dedicated memory devices included in the control circuitry 240.

Still referring to FIG. 7, the process may continue to a decision shown by box 1618, in which the control circuitry 240 determines whether a minimum number of light samples transmitted by the primary light emitter 253 has been received. For example, in a preferred embodiment, the control circuitry 240 determines whether sixteen iterations of activating the primary emitter 253 and detecting the corresponding sixteen electrical signals from the light sensor 258 have been completed. If the minimum number of light samples has not been received, than the control circuitry 240 may activate the primary light emitter 253 again, thereby repeating the steps included in the second iterative step shown by box 1620.

Once the minimum number of light samples has been received, in a step shown by box 1622, the control circuitry 240 determines an average detected value of the primary light emitter samples received. For example, in a preferred embodiment, because the control circuitry 240 receives 16 light samples from the primary light emitter 253, the 16 light samples are added together and the total divided by 16 to determine the average detected value of the primary light emitter samples received. In a preferred embodiment, the determined average value corresponding to light transmitted by the primary light emitter 253 is a floating point value within the range of [0-1] and is stored on one or more dedicated memory devices included in the control circuitry 240.

The process 1600 for to determining whether to sound an occlusion alarm may include an operation that compares the detected value of the light emitted by the primary light emitter 253 with the detected value of the light emitted by the reference light emitter 253. For example, in this embodiment, the step 1624 indicates that the control circuitry 240 compares the average detected value of the light emitted by the primary light emitter 253 (determined by the step shown by box 1622) with the average detected value of the light emitted by the wide-angle reference light emitter 253 (determined by the step shown by box 1612). In one example of this comparison function, the average detected value of the light emitted by the primary light emitter 253 is divided by the average detected value of the light emitted by the wide-angle reference light emitter 255. Also, in particular embodiments, the resulting comparison value is a floating point value within the range of [0-1] and is stored on one more dedicated memory devices included in the control circuitry 240.

In an optional step shown by dashed box 1626, the control circuitry 240 normalized the comparison value determined in the step shown by box 1624. For example, in a preferred embodiment, the floating point comparison value in the range of [0-1] is multiplied by 100, normalizing the comparison value to an integer value in the range of [0-100]. These percentages make up the percentages show in the right axis of FIG. 8A.

Once a percentage is determined, it can be compared to one or more threshold values to determine whether to sound an occlusion alarm in step 1628. As discussed above, thresholds can be variable for the reasons discussed above. Moreover, it in some cases, the percentages calculated in step 1626 or some other comparison coming out of step 1624 can be used to estimate a pressure and/or make other decisions illustrated in FIGS. 10-12, which are discussed above. For example, the process 1600 includes a step 1628 in which the control circuitry 240 determines if the comparison value (e.g., either of the values determined by the step shown by box 1624 or the normalized comparison value determined in the step shown by box 1626) is outside a threshold range (e.g., less than or equal to a minimum threshold value, or greater than or equal to a maximum threshold value, or the like). The process 1600 can be performed immediately prior or immediately after each drive cycle of the pump device 100.

Exemplary Medication Delivery System Having Force Sensor

FIGS. 9A and 9B illustrate an alternative fluid infusion device 900 that includes a force sensor, which can be an insulin infusion device. FIG. 9A is an exploded perspective view and FIG. 9B is a cross-sectional view, which are simplified and does not include all of the elements, components, and features that would be present in a typical embodiment. Like infusion device assembly 15 from FIG. 1, fluid infusion device 900 can automate medication delivery and/or can communicate with a CGM 50, a BGM 70, and/or a remote computing device 60.

Fluid infusion device 900 is designed to be carried or worn by the patient. A fluid infusion device 900 accommodates a fluid reservoir 911 for the fluid to be delivered to the user. A length of tubing 908 is the flow path that couples the fluid reservoir to the infusion set (not shown). A removable cap or fitting 910 is suitably sized and configured to accommodate replacement of fluid reservoirs (which are typically disposable) as needed. In this regard, the fitting 910 is designed to accommodate the fluid path from the fluid reservoir to the tubing 908.

Fluid infusion device includes a housing 912 and a housing end cap 914 that is coupled to an end 916 of the housing 912 to enclose components within the housing 112. These internal components include, without limitation: a battery tube subassembly 918; a sleeve 920; a slide 921; an electronics assembly 922; a drive motor assembly 924 having a drive screw 925; a force sensor 926; and a motor support cap 928. Some components that are located outside the housing 912, namely, a keypad assembly 930 and a graphic keypad overlay 932 for the keypad assembly 930. The keypad assembly 930 and the graphic keypad overlay 932 may be considered to be part of a user interface of the fluid infusion device 900. The outer edge of the motor support cap 928 is attached to the interior side of the housing 912, and the motor support cap 928 contacts the force sensor 926 to remove assembly tolerances from the drive motor assembly 924. Fluid reservoir 111 is inserted into a reservoir cavity defined within the housing 912. The reservoir cavity is configured, sized, and shaped to accommodate fluid reservoirs, and the fluid reservoir 911 is maintained in the reservoir cavity using the fitting 910. The electronics assembly 922 may include a suitably configured electronics module, which may include or cooperate with a power supply, at least one memory element, at least one processor, processing logic, and device software, firmware, and application programs.

FIG. 9B depicts the state of the fluid infusion device 900 after the fluid reservoir 911 has been inserted into the reservoir cavity 934 and after the fitting 910 has been secured to the housing 912 to hold the fluid reservoir 911 in place. While certain embodiments accommodate disposable, prefilled reservoirs, alternative embodiments may use refillable cartridges, syringes or the like. A cartridge can be prefilled with insulin (or other drug or fluid) and inserted into the housing 912. Alternatively, a cartridge could be filled by the user using an appropriate adapter and/or any suitable refilling device.

Force sensor 926 is configured to react in response to force imparted thereto. In this regard, electrical, mechanical, magnetic, and/or other measurable or detectable characteristics of the force sensor 926 vary in accordance with the amount of force applied to the force sensor 926. Accordingly, force sensor 926 can detect forces being applied to the drive system, which is indicative of a pressure in the fluid reservoir 911. FIG. 8C depicts a possible curve 850 that correlates detected forces in a drive system to unit increments of medication forced into a fully occluded infusion set. Accordingly, the methods described herein can be implemented on the fluid infusion device 900 and systems including it.

Force sensor 926 might implement or otherwise leverage known sensor technologies, such as the sensor technology described in U.S. Pat. No. 6,485,465. As shown in FIG. 9A, the force sensor 926 includes at least one electrical lead 954 that is electrically coupled to the electronics module (or controller) of the fluid infusion device 900. Alternatively, the force sensor 926 could use wireless data communication technology to provide force-related data to the electronics module. In certain implementations, the force sensor 926 is suitably configured to indicate or generate a plurality of different output levels that can be monitored and/or determined by the electronics module. In practice, the output levels obtained from the force sensor 926 are initially conveyed as analog voltages or analog currents, and the electronics module includes an analog-to-digital converter that transforms a sampled analog voltage into a digital representation. Conversion of sensor voltage into the digital domain is desirable for ease of processing, comparison to threshold values, and the like.

When assembled as shown in FIG. 9B, the drive motor assembly 924 is located in the housing 912. The force sensor 926 is operatively associated with the drive motor assembly 924. For this particular embodiment, the force sensor 926 is coupled to the drive motor assembly 924, and it is located between a base end of the drive motor assembly 124 and the motor support cap 928. In one implementation, the force sensor 926 is affixed to the base end of the drive motor assembly 124 such that the force sensor 126 reacts when it bears against the motor support cap 928. In another implementation, the force sensor 926 is affixed to the housing end cap 914 such that the force sensor 926 reacts when the drive motor assembly 924 bears against the force sensor 926. This configuration and arrangement of the drive motor assembly 924 and the force sensor 926 allows the force sensor 926 to react to forces imparted thereto by the drive motor assembly 924 and/or forces imparted to the drive motor assembly 924 via the fluid pressure of the fluid reservoir 911.

The drive motor assembly 924 includes an electric motor 936 that is actuated and controlled by the electronics module of the fluid infusion device 900. The motor 936 can be realized as a stepper motor that rotates in a stepwise or discrete manner corresponding to the desired number of fluid delivery strokes. Alternatively, the motor 936 could be a DC motor, a solenoid, or the like. The motor 936 may optionally include an encoder (rot shown), which cooperates with the electronics module of the fluid infusion device 100 to monitor the number of motor rotations or portions thereof. This in turn can be used to accurately determine the position of the slide 921, thus providing information relating to the amount of fluid dispensed from the fluid reservoir 911.

The drive motor assembly 924 can be mounted in the housing 912 using an appropriate mounting feature, structure, or element. Alternatively, the mounting could be accomplished using a shaft bearing and leaf spring or other known compliance mountings. The illustrated embodiment of the drive motor assembly 924 includes a drive member (such as the externally threaded drive gear or drive screw 925) that engages an internally threaded second drive member (such as the slide 921) having a coupler 942. The coupler 942 may be attached to or integrated with the slide 921, The slide 921 is sized to fit within the housing of the fluid reservoir 911, which enables the slide 921 to operatively cooperate with the fluid reservoir 911. The fluid reservoir 911 includes a plunger or piston 944 with at least one sealing element or feature (e.g., one or more O-rings, integral raised ridges, or a washer) for forming a fluid and air tight seal with the inner wall of the fluid reservoir 911. As mentioned previously, the fluid reservoir 911 is secured into housing 912 the housing 912 with the fitting 910, which also serves as the interface between the fluid reservoir 911 and the infusion set tubing 908. For this embodiment, the piston 944 is in contact with a linear actuation member, such as the slide 921. For example, the piston 944 may have a female portion 946 that receives the coupler 942 carried by the slide 921. The female portion 946 is positioned at the end face of the piston 944, and it is sized to receive and accommodate the coupler 942. In certain embodiments, the female portion 946 includes a threaded cavity that engages external threads of the coupler 942.

Referring to FIG. 9B, rotation of the drive shaft of the motor 936 results in corresponding rotation of the drive screw 925, which in turn drives the slide 921 via the threaded engagement. Thus, rotation of the drive screw 925 results in axial displacement of the slide 921 and, therefore, axial displacement of the coupler 942. Such displacement of the coupler 942 moves the piston 144 (upward in FIG. 9B) to deliver a predetermined or commanded amount of medication or liquid from the fluid infusion device 900, which corresponds to a unit increment in FIG. 8C. In this manner, the drive motor assembly 924 is configured to regulate delivery of fluid by actuating the piston 944 (under the control of the electronics module and/or control system of the fluid infusion device 900). As described above, if a stepper motor is employed, then the drive motor assembly 924 can regulate delivery of fluid from the fluid infusion device 900 in discrete actuation or delivery strokes (which can be the unit increments noted in relationship to FIG. 8C). The fluid infusion device 900 can employ the sleeve 920 or an equivalent feature (such as an anti-rotation key) to inhibit rotation of the drive motor assembly 924, which might otherwise result from torque generated by the motor 936. In some embodiments, the drive shaft of the drive motor assembly 924, the drive screw 925, and the slide 921 are all coaxially centered within the longitudinal axis of travel of the piston 944. In certain alternative embodiments, one or more of these components may be offset from the center of the axis of travel and yet remain aligned with the axis of travel, which extends along the length of the fluid reservoir 911.

In particular embodiments, the force sensor 926 is realized as an electromechanical component having at least one variable resistance that changes as the force applied to the force sensor 926 changes. In alternative embodiments, the force sensor 926 is a capacitive sensor, a piezoresistive sensor, a piezoelectric sensor, a magnetic sensor, an optical sensor, a potentiometer, a micro-machined sensor, a linear transducer, an encoder, a strain gauge, or the like, and the detectable parameter or characteristic might be compression, shear, tension, displacement, distance, rotation, torque, force, pressure, or the like. In practice, changing characteristics of the force sensor 926 are associated with output signal characteristics that are responsive to a physical parameter to be measured. Moreover, the range and resolution of the monitored output signal provides for the desired number of output levels (e.g., different states, values, quantities, signals, magnitudes, frequencies, steps, or the like) across the range of measurement. For example, the force sensor 926 might generate a low or zero value when the applied force is relatively low, a high or maximum value when the applied force is relatively high, and intermediate values when the applied force is within the detectable range.

A number of embodiments of the invention have been described. Nevertheless, it will be understood that various modifications may be made without departing from the spirit and scope of the invention. Accordingly, other embodiments are within the scope of the following claims.

What is claimed is:

1. A method of operating a portable infusion pump system, the method comprising:

initiating a dispensation of an infusion fluid by a pump of the portable infusion pump system;

identifying an intended dispensation time at which the dispensation of the infusion fluid is initiated;

detecting, at multiple times during a dispensation period of time, pressure measurements of the infusion fluid in an infusion fluid pathway of the pump;

identifying pressure data predetermined for the infusion pump system, the pressure data indicative of a pressure change of the infusion fluid pathway in an occluded condition, the pressure data including one or more threshold pressure values;

comparing each of pressure measurements detected at the multiple times during the dispensation period to the one or more threshold pressure values; and determining, based on one or more of the detected pressure measurements exceeding the one or more of the threshold pressure values of the pressure data, that the dispensation occurred at an actual dispensation time that is delayed from the intended dispensation time due at least in part to the occluded condition; and determining an amount of the infusion fluid delivered from the actual dispensation time.

2. The method of claim 1, wherein the infusion fluid is insulin.

3. The method of claim 2, wherein control circuitry of the infusion pump system calculates an estimate of insulin-on-board based on the amount of the infusion fluid delivered from the actual dispensation time.

4. The method of claim 2, further comprising receiving, from a blood glucose detection device, at least one blood glucose level, wherein an amount of insulin in the dispensation is determined based at least in part upon the at least one blood glucose level and an estimate of insulin-on-board.

5. The method of claim 4, wherein the one or more pressure threshold values include a variable alarm threshold, the method further comprising outputting an occlusion alarm if one or more of the detected pressure measurements exceeds the variable alarm threshold, the variable alarm threshold being dependent upon at least one detected blood glucose value.

6. The method of claim 5, wherein the variable alarm threshold is further dependent on a timing of one or more recent dispensations, amount of one or more recent dispensations, type of one or more recent dispensations, or a combination thereof.

7. The method of claim 2, further comprising predicting a future blood glucose level based on the actual dispensation time and the amount of the infusion fluid delivered from the actual dispensation time.

8. The method of claim 2, further comprising determining an amount of insulin that is stuck in transit in the infusion fluid pathway of the pump due to the occluded condition based on the pressure data, wherein the actual dispensation time is determined based on a time that the detected pressure decreases to a predetermined level, wherein an amount of insulin stuck in transit is excluded from an insulin-on-board calculation performed by control circuitry of the portable infusion pump system.

9. The method of claim 1, wherein, in response to determining that the dispensation occurred at an actual dispensation time that is after the intended dispensation time, delaying or reducing a subsequent dispensation of the infusion fluid.

10. The method of claim 1, wherein the pressure level is determined or estimated using a pressure sensor or a force sensor.

* * * * *